US010653385B2

(12) United States Patent
Mehendale et al.

(10) Patent No.: US 10,653,385 B2
(45) Date of Patent: May 19, 2020

(54) TUBE ALIGNMENT FUNCTIONALITY FOR MOBILE RADIOGRAPHY SYSTEMS

(71) Applicant: KONINKLIJKE PHILIPS N.V., Eindhoven (NL)

(72) Inventors: Aditya Mehendale, Eindhoven (NL); Richard Johannes Maria Van De Ven, Eindhoven (NL); Dirk Manke, Hamburg (DE); Christoph Kurze, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 573 days.

(21) Appl. No.: 14/909,625

(22) PCT Filed: Jul. 21, 2014

(86) PCT No.: PCT/EP2014/065570
§ 371 (c)(1),
(2) Date: Feb. 2, 2016

(87) PCT Pub. No.: WO2015/018629
PCT Pub. Date: Feb. 12, 2015

(65) Prior Publication Data
US 2016/0183909 A1    Jun. 30, 2016

(30) Foreign Application Priority Data

Aug. 5, 2013  (EP) .................................... 13179281
Oct. 18, 2013  (EP) .................................... 13189318

(51) Int. Cl.
*A61B 6/00* (2006.01)
*A61B 6/08* (2006.01)

(52) U.S. Cl.
CPC ................ *A61B 6/587* (2013.01); *A61B 6/08* (2013.01); *A61B 6/4405* (2013.01);
(Continued)

(58) Field of Classification Search
CPC ..... A61B 6/4405; A61B 6/4452; A61B 6/461; A61B 6/587; A61B 6/588; G01S 5/021; G01S 5/242
See application file for complete search history.

(56) References Cited

U.S. PATENT DOCUMENTS

| 4,752,948 A | 6/1988 | MacMahon |
| 5,241,578 A | 8/1993 | MacMahon |

(Continued)

FOREIGN PATENT DOCUMENTS

| DE | 102010008551 A1 | 8/2011 |
| DE | 102010008552 A1 | 8/2011 |

(Continued)

*Primary Examiner* — Dani Fox
*Assistant Examiner* — Soorena Kefayati
(74) *Attorney, Agent, or Firm* — Larry Liberchuk

(57) ABSTRACT

An X-ray imager has a navigation-aid subsystem including one or more transmitters (TX), one or more receivers (RX) and one or more reflectors (RFL). A radio signal is transmitted by transmitter (TX), is then reflected off reflector RFL and is then received at receiver (RX). The received signal is then resolved into positional correction information that can be used to guide a motion of the imager's tube (S) and or detector (D) to position and/or align the tube (S) and/or detector (D) relative to each other in a desired spatial configuration to ensure optimal imaging results. The imager may be a mobile imaging system with the detector (D) portable.

12 Claims, 12 Drawing Sheets

(52) U.S. Cl.
CPC ............ *A61B 6/4452* (2013.01); *A61B 6/461* (2013.01); *A61B 6/588* (2013.01)

(56) References Cited

U.S. PATENT DOCUMENTS

| | | | |
|---|---|---|---|
| 6,435,715 B1 * | 8/2002 | Betz | A61B 6/4458 378/197 |
| 7,014,362 B2 | 3/2006 | Beimier | |
| 7,319,396 B2 | 1/2008 | Homanfar | |
| 7,581,884 B1 | 9/2009 | Barnes | |
| 7,581,885 B2 | 9/2009 | Ertel | |
| 7,639,205 B2 * | 12/2009 | Kudou | H01Q 1/50 343/700 MS |
| 7,654,739 B2 * | 2/2010 | Lumma | A61B 6/06 378/116 |
| 7,677,800 B2 * | 3/2010 | Agano | A61B 6/4429 378/205 |
| 7,744,279 B2 | 6/2010 | Heath | |
| 7,780,350 B2 * | 8/2010 | Tranchant | G05B 19/401 378/205 |
| 7,798,710 B1 | 9/2010 | Barnes | |
| 7,806,591 B2 * | 10/2010 | Wang | A61B 6/00 378/196 |
| 7,817,040 B2 | 10/2010 | Homanfar | |
| 7,873,145 B2 * | 1/2011 | Liu | G03B 42/02 378/98.8 |
| 7,896,547 B2 * | 3/2011 | Kito | A61B 6/4283 378/205 |
| 7,988,357 B2 * | 8/2011 | Hornung | A61B 6/4233 378/197 |
| 8,013,783 B2 * | 9/2011 | Lomes | H01Q 3/267 342/165 |
| 8,072,328 B2 | 12/2011 | Ando | |
| 8,115,594 B2 | 2/2012 | Koezuka | |
| 8,821,015 B2 * | 9/2014 | Stagnitto | A61B 6/4291 378/205 |
| 8,823,598 B2 * | 9/2014 | Beausang | H01Q 1/246 343/817 |
| 9,055,923 B2 * | 6/2015 | Berger | A61B 6/4494 |
| 9,107,643 B2 * | 8/2015 | Chang | A61B 6/5258 |
| 9,138,195 B2 * | 9/2015 | Krupica | G01N 23/046 |
| 9,184,822 B2 * | 11/2015 | Whitaker | H01Q 3/2605 |
| 2002/0150214 A1 | 10/2002 | Spahn | |
| 2006/0109958 A1 | 5/2006 | Ertel | |
| 2006/0280293 A1 | 12/2006 | Hardesty | |
| 2006/0285641 A1 | 12/2006 | Scherch | |
| 2009/0032744 A1 * | 2/2009 | Kito | A61B 6/4233 250/580 |
| 2009/0052618 A1 | 2/2009 | Homanfar | |
| 2009/0257564 A1 | 10/2009 | Kito | |
| 2010/0123083 A1 | 5/2010 | Petrick | |
| 2011/0249793 A1 | 10/2011 | Lalena | |
| 2011/0305319 A1 | 12/2011 | Liu | |
| 2012/0307965 A1 * | 12/2012 | Bothorel | A61B 6/14 378/10 |
| 2013/0051528 A1 * | 2/2013 | Inglese | A61B 6/08 378/62 |
| 2013/0127613 A1 | 5/2013 | Zhang | |
| 2013/0129048 A1 * | 5/2013 | Chicchetti | H05G 1/08 378/62 |
| 2014/0112439 A1 * | 4/2014 | Berger | A61B 6/4494 378/62 |
| 2014/0247918 A1 * | 9/2014 | Kang | A61B 6/4452 378/62 |
| 2014/0276056 A1 * | 9/2014 | Ohta | A61B 6/465 600/440 |
| 2015/0117603 A1 * | 4/2015 | Keeve | A61B 6/0407 378/62 |
| 2016/0218673 A1 * | 7/2016 | Anderson | H03D 7/14 |
| 2017/0363729 A1 * | 12/2017 | DiPoala | G01S 13/04 |

FOREIGN PATENT DOCUMENTS

| | | |
|---|---|---|
| EP | 2617359 A1 | 7/2013 |
| JP | 2009050693 A | 3/2009 |
| WO | 2008023301 A1 | 2/2008 |

* cited by examiner

TUBE ALIGNMENT FUNCTIONALITY FOR MOBILE RADIOGRAPHY SYSTEMS

CROSS-REFERENCE TO PRIOR APPLICATIONS

This application is the U.S. National Phase application under 35 U.S.C. § 371 of International Application No. PCT/IB2014/065570, filed on Jul. 21, 2014, which claims the benefit of European Patent Application No. 13179281.4, filed on Aug. 5, 2013 and European Patent Application No. 13189318.2, filed on Oct. 18, 2013. These applications are hereby incorporated by reference herein.

FIELD OF THE INVENTION

The invention relates to an imaging system, to a related method, to a computer program element, and to a computer readable medium.

BACKGROUND OF THE INVENTION

Medical personnel in intensive care units or in A & E (Accident and Emergency) departments have come to rely more and more on mobile X-ray imagers for flexible radiography. Mobile X-ray imagers afford acquisition of X-ray images even under awkward, adverse conditions or can be used in different locations. The imager is in other words not permanently installed in a particular X-ray examination room or location as more traditional imaging systems are. Another use scenario for mobile X-ray imagers is for instance in care homes. Elderly patients who have been bed-ridden for long will need to have a chest X-ray taken, sometimes every day, to monitor for possible build-up of water in their lungs which could lead to pneumonia.

It has been however noted that, on occasion, such mobile imagers do not live up to expectations in terms of image quality and/or incurred radiation dosage.

A mobile X-ray imager is described in Applicant's WO2008/023301.

SUMMARY OF THE INVENTION

There may therefore be a need for alternative X-ray systems to address at least the above mentioned deficiency.

The object of the present invention is solved by the subject matter of the independent claims where further embodiments are incorporated in the dependent claims. It should be noted that the following described aspects of the invention equally apply to the related method, to the computer program element and to the computer readable medium.

According to a first aspect of the invention there is provided an imaging system comprising:

an imaging apparatus having an X-ray source and a detector (referred to herein as the "tube-detector (sub-) system") for receiving X-ray radiation emittable from said source, the X-ray source movable relative to the detector or the detector movable relative to the X-ray source;

a transmitter for transmitting a radio signal;
a reflector configured to reflect said radio signal;
a receiver for receiving said reflected radio signal;
a transducer operative to convert the received radio signal into positional correction information suitable to guide a motion of the X-ray source or of the detector so as to achieve a spatial configuration of X-ray source ("tube") and detector, where the X-ray source and the detector are in alignment and/or are at a predefined distance from each other.

In other words, as proposed herein the imaging system ("imager") is equipped with a "beacon" navigation subsystem to aid the user to adjust the spatial configuration of the tube-detector system. The navigation subsystem may be fitted as an add-on to existing imaging apparatuses, in particular mobile X-ray imaging apparatuses, or other, permanently installed ones, where the detector is portable, so there is no rigid mechanical connection between tube and X-ray source, in other words, the mutual spatial configuration is not known a priori.

The positional correction information generated by transducer is such that it measures or is indicative of a spatial "deviation" from a desired, target spatial configuration of the tube-detector system. Depending on the desired level of detail, the positional correction information merely indicates that a correction is needed, that is, that the current tube/detector system does not have the desired spatial configuration. This information can be used manually by the user or can be fed into a control equipment, to vary the current configuration in a "trial-and-error" manner to so move tube or detector towards the desired spatial configuration. At the next level of detail, the positional correction information also indicates the orientation/direction in which the detector needs to be rotated or shifted in order to move closer to the desired spatial configuration. Finally, at yet a higher level of detail, the positional correction information is indicative of not only the orientation/direction but also of the amounts by which tube or detector needs to be shifted or rotated to achieve the desired spatial configuration. The desired level of detail, in respect of the positional configuration information, is defined by the number of transmitters/receivers and or reflectors used. It is contemplated herein that even if the system is equipped to supply a higher level of detail in respect of the positional correction information, such a system can still be adjusted to supply only a lower level of positional correction information.

Because the system proposed herein operates on radio waves and not on visible light, there is no line of sight required between the detector and the tube, thereby addressing the problem indicated earlier that, especially in mobile X-ray system applications, the detector is usually not visible because of optical occlusion by the patient's body or object. Precise positioning and alignment (rotation and/or centration) can be achieved. This translates into a) less grid artifacts (if an anti-scatter grid is used with the detector) due to misalignment, b) higher image quality and therefore overall c) into an improved clinical workflow because of fewer retakes. For instance, proper alignment will help minimize the amount of shadow cast by the anti-scatter grid. Precise tube-detector system alignment may also be beneficial when a collimator is used to collimate the X-ray beam, because such collimator is usually positioned at the tube. It is envisaged herein that the frequency for the radio wave signal is in the kHz-MHz range. In particular for medical application, the frequency range is in the hundreds of kHz range or is in the low MHz range, such as 1 or 2 MHz or in between 1 or 2 MHz. In non-medical X-ray applications, higher frequencies in the higher MHz range may be used (for instance, baggage screening or non-destructive industrial material testing, etc).

"Being in alignment" in the present context means that, when the imaging apparatus is in operation, a center beam of the X-ray beam is orthogonally incident on the detector's image plane at a center point of said image plane. In some embodiments, there is also rotational alignment to align (around an axis perpendicular to the detector plane), either the detector or the tube.

In one embodiment, the predefined distance is the required source-detector distance (SID) for the intended image acquisition, which is usually known and is a function of the detector type and, in particular, is a function of the type of anti-scatter grid used with the detector.

In one embodiment, the reflector(s) is (are) passive. In this context "passive" means the reflector has no autonomous or stand-alone "on-board" power-supply (other than one or more capacitors), like batteries, scavengers, etc. for the purpose of metrology. Also, in one embodiment, there is no on-board IC "chip" to generate data other than the reflected off signal. In particular this means, that, in some embodiments, for metrology purposes, there is no data connection (signal cables etc.) running from the reflectors to the outside of the reflector. No autonomous signal generation occurs in the reflector, but the received power or signal is merely reflected off. In one embodiment, there is no memory element in the reflector. In one embodiment, where a plurality of reflectors is used, there are embodiments envisaged where not all the reflectors are passive but there are one or more active ones. In a preferred embodiment, all reflectors are indeed passive. Using passive (even disposable) reflectors affords a cost effective solution for the tube-detector adjustment challenge. In some embodiments, the reflectors may be all active, however.

In one embodiment, transmitter and receiver are not spatially separated components, but are combined into a transceiver, or are arranged in a common housing or on a common circuit board or similar.

According to one embodiment, the reflector and/or detector is movable with the X-ray source and/or detector motion. In one embodiment, adjusting a spatial configuration of tube-detector system includes changing tube's distance and or alignment relative to detector's radiation sensitive surface. The position and orientation of the detector is fixed in some use scenarios although this may not always be so and in some cases it is the detector whose position and alignment is adjusted relative to the tube and it is the tube that is fixed during the adjustment. However, in some embodiments, both, tube and detector, are movable to effect adjusting for the spatial configuration.

In one embodiment, the transceiver and/or transmitter and/or the receiver are arranged at the X-ray tube, whereas the one or more reflectors are arranged at the detector. However, the reverse arrangements is also envisaged herein, that is, the reflector(s) is (are) arranged at the tube and it is the transceiver and/or transmitter and/or receiver that is arranged at the detector. "Arranged at the X-ray source" means arranged at an X-ray source assembly, for instance by integration in an X-ray tube housing or by placement on the housing. However, in some embodiments, at least the transmitter or receiver are otherwise placed, that is, away from X-ray source, elsewhere at the imager body, so as to have a defined spatial positional relationship with the X-ray source. It is even envisaged in one embodiment, that transceiver and/or transmitter and/or the receiver are placed away from the imager body and are installed at a known location in a room. The navigation system can then be used after "registering" the imager with the local transceiver and/or local transmitter and/or the local receiver pre-installed in said room before attending to adjust the tube-detector configuration. A set of transceiver and/or transmitter and/or the receiver can then be used for different imagers by sharing the transceiver and/or transmitter and/or the receiver. Registration in this embodiment, means that the relative position/distance/orientation between the fixed transceiver and/or transmitter and/or the receiver are registered and a corresponding offset is applied to the positional correction information in order to account for this distance.

According to one embodiment,
i) the transmitter is so tuned and/or
ii) the reflector and the receiver and/or the reflector and the transmitter are mutually oriented in space in such a manner and/or are at such distance relative to each other
that the radio signal is no longer reflected by the reflector (RFL) and/or is no longer received at the receiver (RX) when the X-ray source and the detector are aligned and/or are at the predefined distance.

In this embodiment, the positional correction information generated by the transducer is suitable for guiding the X-ray source or detector motion so as to achieve a decrease in signal strength of the reflected radio (as received at the receiver or transceiver) signal down to substantially zero. This navigational concept may be referred to as the "dead zone" or "null response" seeking concept. The lack of the reflector's response (that is, said "null response") as used in this embodiment, is due to i) mutual orthogonality of reflectors versus receiver and/or transmitter (or, when combined, the transceiver) or ii) is due to the tuning of the transmitter current and/or of the physical spatial arrangement of transmitter and/or receiver and/or transceiver.

As to ii), because of orthogonality, a current in transmitter can no longer induce response in reflector thereby bringing the response signal strength down to essentially zero or lower than a sensitivity threshold when tube-detector system assumes the spatial target configuration.

As to i), the tuning causes the formation of "deadzones" in the magnetic flux pattern of the transmitter/receiver/transceiver. The deadzones are loci (a point, a plane or a line in space) where there is essentially zero magnetic flux caused, or the magnetic flux is at least zero in the sensitive-direction of the reflector placed there.

In other words, there is null response from reflector at receiver when the imager's source-detector system is aligned and/or X-ray source and detector are the required distance apart. In yet other words, the navigation sub-system allows seeking out a null response to find the targeted spatial configuration. The null zone or the null response can be sought out by physically moving (at least parts of) the transceiver, or, when separately arranged, the receiver or transmitter, or the reflector. Alternatively or additionally to said physical motion, the null zone or the null response can be sought out by "electrically shifting" the dead-zones themselves by tuning (that is, energizing) the transmitter/transceiver by changing amplitude and phase combination of the current or currents that feed the transceiver(s) or transmitter(s). This "electrically" shifting of the deadzone position(s) allows searching over a wider area for the presence of reflectors. Transmitter/receiver is so tuned that essentially no reflector signal is picked up by the receiver once the target (spatial) configuration of X-ray source and detector is assumed. In other words, the computed positional correction information furnishes "guide posts" to guide the source-detector system towards the targeted spatial configuration.

This dead zone embodiment allows adjusting the tube detector system without measurement of a specific, non-zero signal strength. The null response seeker and/or the dead-zone concept allows using relatively low frequencies (which is desirable for medical applications), and one still is able to resolve for alignment (that is, rotation and/or centration) and distance within a few degrees range and mm-range, respectively.

In one embodiment, the "deadzone" or "null response seeking" embodiment is achieved by strategically placing, initially, in a set-up phase, the transmitter(s)/receiver(s)/transceiver(s) relative to the one or more reflectors in such a spatial manner that the mutual orientation between receiver(s) versus reflectors is orthogonal precisely in the desired spatial configuration of the tube-detector system. This type of initial setup in respect of the receivers/reflector placements may also required in other embodiments that are not based on the dead zone or "orthogonality seeking" navigation principle.

According to one embodiment, the positional correction information is supplied by the transducer in a data stream (in one embodiment in "real time") to update the positional correction information whilst the X-ray source or detector is being moved, either automatically or manually by a user.

According to one embodiment, the imaging system further comprises: i) an actuator to effect motion of the X-ray source or detector; and a controller to control operation of the actuator and to control the motion of X-ray source or detector, wherein the controller operates in response to and in dependence on the positional correction information in order to achieve the desired spatial configuration. This embodiment allows automatically changing tube and detector position/orientation when seeking out the desired spatial configuration. The controller is either closed-loop or is "feed-forward" (open loop) to move either X-ray source or detector so that the target spatial configuration is assumed. The change in configuration is either effected automatically (that is, without user input) or is effected semi-automatically, in the sense that the controller responds to user issued commands from a "remote control unit" or similar.

According to one embodiment, the X-ray source is configured to be moved manually by a human operator. In other words, the system is a "grab-and-drag" system. For instance, in one embodiment, an X-ray source housing is arranged on an articulated arm and the housing has a handle or other grip option to conveniently allow operator to move about X-ray source manually to position the X-ray housing and hence the X-ray tube. In the embodiment where the detector is movable, it is the detector body that is furnished with said handle or grip option.

According to one embodiment, the system further comprises a display unit for displaying the positional correction information or the updated positional correction information.

According to one embodiment, the reflector is one of a plurality of reflectors each configured to resonate at a different frequency, wherein the transmitter is configured to transmit the radio signal at the different frequencies. This allows increasing the level of detail sought with respect to the positional correction information as mentioned earlier. A single reflector, on the other hand, would be able to resolve for 5 degrees of freedom (DoFs) at the most. This may be sufficient for some embodiments where no rotation is required. Using a plurality of reflectors that each responds to a unique frequency allows implementing a "reality check" by interrogating for the presence, if any, of the detector and, in one embodiment, even for the type of detector in use. According to one embodiment, the reflectors each have a different orientation when the X-ray source and the detector are in alignment at the predefined distance.

According to one embodiment, the transmitter is one of a plurality of transmitters. In one embodiment, each transmitter has a different position or orientation, fixed or variable, with respect to each other. This allows forming the null field or dead zone (where no signal is received from reflector at the receiver) at a required distance.

Other combinations are also envisaged. In one embodiment, there is a single reflector and multiple transmitters or transceivers. In one embodiment, there is a single transmitter and multiple receivers and one or more reflectors.

According to one embodiment, the plurality of transmitters (or transceivers) is arranged as a phased array. This allows for compact integration of transmitters in the tube housing. In one embodiment the array is formed around the X-ray tube's focal spot. This phased array embodiment in combination with more than two reflectors allows resolving the signals of positional correction information for each of the 6 DoFs of X-ray source and/or detector.

According to one embodiment, the system further comprises a prompter configured to issue any one or a combination of a visual, haptic/tactile or audio/acoustic prompter signal for a human operator of the imaging apparatus, wherein the signal is issued in dependence on the positional correction information and is issued whilst the X-ray source or the detector is being moved to assume the spatial configuration or is issued once said spatial configuration is assumed. For instance, in the latter case, a sound or visual signal is issued only when the desired spatial configuration of the tube-detector system is assumed after moving tube and/or detector accordingly.

According to one embodiment, the prompter signal is modulated according to the positional correction information. For instance, in one embodiment, an audio signal such as a "chirp or a beep" changes pitch, or a sequence, or intensity or another sensory attribute, the closer a current rube-detector configuration comes to the target spatial configuration or, in one embodiment, as one approaches the dead zone. The information furnished by the modulation signal in one embodiment is not unlike the positional information given in children games such "Buckle Buckle beanstalk" or "hot or cold": when at certain position, one does not know a priori which way to move. Rather it is by trial-and-error when observing how the modulated prompter signal changes that one derives clues for the right direction towards the desired optimal tube-detector spatial configuration. If a plurality of transmitters/receivers are used, the signal can afford more positional detail, because now the movement direction can also be included in the modulated signal. For instance, the movement direction can be indicted by sound or visual symbology (such as by graphical arrows on a display) whether a shift to, say, the left or right is required or whether to rotate clockwise or counterclockwise, etc.

According to one embodiment, at least one of the transmitter or the receiver is attached to the X-ray source or at least one of the transmitter or the receiver is situated away from the X-ray source.

According to one embodiment, the reflector is attached to the detector or is attached to the X-ray source.

According to one embodiment, the imaging apparatus is mobile and/or the detector is of the portable type.

The invention is applicable for mobile radiography systems and for free exposures at fixed radiography systems. It may also be applied to any system whereby two objects need to be aligned in one or more DoFs, and where it is desirable to have one of the two objects passive.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
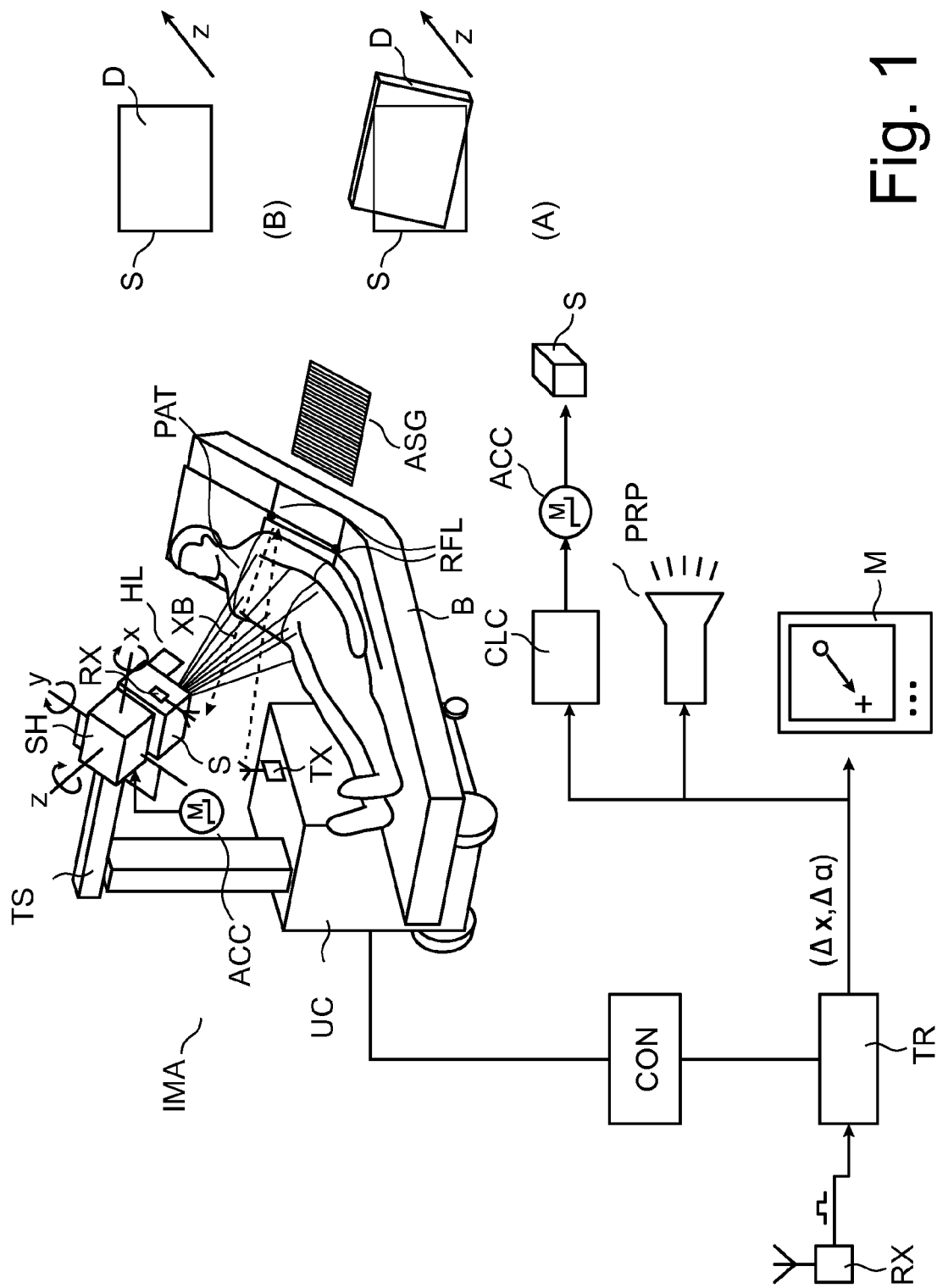
FIG. 1 shows a mobile radiography system including a navigation aid subsystem.

With reference to FIG. 1 there is shown an arrangement including a mobile X-ray imaging apparatus IMA. According to one embodiment, the apparatus is of the "dolly type" and comprises an undercarriage UC on rollers so as to be position-able at a convenient location relative to a patient PAT. The imager IMA is mobile in the sense that it is not permanently installed at a fixed place such as a room, but can be moved about from location to location as desired. One possible clinical application (as exemplary indicated in FIG. 1) is bedside chest X-ray but other uses are also envisaged for instance, in A&E, where X-ray images are frequently required of other body parts such as a patient's hand, foot, leg or head if an examination for injuries is called for.

There is an operator console CON built into the undercarriage for clinical personnel (in the following referred to as operator or user) to operate imager EMA. Console CON allows user to control image acquisition by releasing individual X-ray exposures, for example by actuating a joystick or pedal or other suitable input means coupled to said console CON.

The console CON also includes a display unit M for viewing acquired X-ray images or for displaying a user interface to aid user when operating the mobile X-ray apparatus IMA.

The basic components of the imager are an X-ray tube S (arranged in a housing SH) and a mobile or portable detector D. During an imaging run, the detector D receives radiation emitted by said tube S after passage of said radiation through a relevant body part of patient PAT. The detector D together with the X-ray tube ("tube") S will be occasionally referred to herein at the "tube-detector (sub-)system".

In one embodiment, the portable detector D is a relatively flat, slab or plate-like object with a housing or frame. The detector has a radiation sensitive imaging surface (which in some embodiments is planar) formed of an array of detector cells. Each cell responds to the radiation emitted from the X-ray source as will be described in more detail below. In one embodiment, the detector unit D is rectangular in shape measuring about 30 cm×40 cm in the x,y plane with a thickness in z direction of about 3-5 cm or less, but other shapes are also envisaged herein. The radiation sensitive area is in one embodiment surrounded by a border portion which forms part of the housing. The mobile detector D may be a film cassette or a fully digitalized unit. In one embodiment, the detector D is capable of communicating with the X-ray apparatus operating console via wireless connection to transmit the detected image (projection raw) data to the console for image processing. The console and the mobile detector include suitable wireless interfaces to do this. A simpler, wired embodiment is also envisaged however, where communication between detector D and imager is via a wired socket connection. In some embodiments, an anti-scatter grid (ASG) is used. An ASG is essentially a grid-like structure formed from small vanes or "fins" extending away from and perpendicular to detector surface. The ASG, when mounted, covers essentially all the detector surface.

The actual image acquisition proceeds broadly as follows: during an image acquisition, an X-ray beam XB emanates from the X-ray tube S, passes (after a possible collimation by the collimator) through the patient PAT at a region of interest, experiences attenuation by interaction with matter therein, and the so attenuated beam XB then strikes the detector's surface at a plurality of the detector cells. Each cell that is struck by an individual ray (of said beam XB) responds by issuing a corresponding electric signal. The collection of said signals is then translated by a data acquisition system ("DAS"—not shown) into a respective digital value representative of said attenuation. The density of the organic material making up the ROI (region of interest), for example rib cage and cardiac tissue, determines the level of attenuation. High density material (such as bone) causes higher attenuation than less dense materials (such as the cardiac tissue). The collection of the so registered digital values is then consolidated into an array of digital values forming an X-ray projection image for a given (field of view) FoV setting.

An important preparatory procedure prior to the actual image acquisition is the spatial adjustment of the tube-detector system for a desired spatial configuration. Such configuration depends on the imaging task at hand, for instance, depending on the physique of the patient. The configuration is defined in particular by i) a specific distance between the tube S and the detector D (source-image-distance (SID)) and ii) an alignment of the orientation of the tube S to or with the image sensitive surface of the detector D. In other words, the specific spatial configuration defines a mutual spatial relationship between the detector and the tube, which is necessary to achieve optimal images. There is in general only a single one such optimal spatial tube-detector system configuration. For instance, using an ASG calls for alignment errors (when occurring individually) of less than ~3° for orientation (roll, yaw, pitch), and an off-axis error of less than ~7 cm. If said errors occur in combination, the error margins are even stricter. Not observing those margins when operating with an ASG may cause unwanted grid artifacts in the images and may require higher dosage as the desired primary radiation is partially blocked too. To mitigate image artifacts, the SID error should be less than 40 cm. However, since the SID has a strong influence (because of the $1/r^2$-law) on the actually applied X-ray dose, the SID error should preferably be not greater than 10 cm in clinical practice to reduce dosage.

To address this requirement for spatial adjustment, the mobile X-ray apparatus IMA includes in one embodiment an X-ray tube positioning mechanism TS. Said mechanism allows movement of the X-ray tube XR substantially along each spatial direction x,y,z of a reference frame and rotation around each direction x,y,z to adjust any one or a combination of pitch, roll, yaw, thereby affording a positional adjustment with 6 degrees of freedom (DoF), with the tube considered a rigid body in 3D space. This is indcted by the local coordinate system with origin at the tube S's focal point with the respective rotation options, indicated by rounded arrows. The X-ray tube S positioning mechanism TS is implemented in one embodiment as an articulated arm that attaches for one of its ends to the undercarriage UC and the other end carries the X-ray tube in its housing. In other words, said tube positioning mechanism is movable relative to the X-ray apparatus undercarriage UC. The articulated arm is only an exemplary embodiment and purely track based solutions are also envisaged. In one embodiment of a track-based solution there are a system of tracks that run along beams or poles, and the tube S is slidable along one of the tracks, and the beams themselves can be slidably translated across others of the beams to so effect positional adjustment along x,y,z. The poles or beams are rotatable around their longitudinal axis and/or the tube is attached to its carrying arm via a ball joint to afford adjustability of pitch and/or roll and/or yaw. In other words, any mechanical arrangement that affords spatial adjustment of the tube and/or its focal spot at up to 6 DoFs is contemplated herein. However this does not mean that the X-ray tube positioning mechanism must in any embodiment, by necessity, afford adjustment for all the 6 DoFs, but simpler systems are also envisaged herein where adjustment options are (more) restricted. For example, some systems may allow only planar adjustments of the tube S along the x,y axis with no rotation option of the tube, or rotation is only around the z axis to adjust yaw but not pitch or roll, etc.

As shown in FIG. 1, the housing includes a handle H for manually positioning the position of the tube XR in space. In one embodiment, the user grabs the X-ray tube housing by said handle HL and "drags" it to the required position relative to the patient PAT and, in particular, relative to the detector's position/orientation. A motorized embodiment is also envisaged, in which there are arranged a number of suitable mechanical actuators M, such as stepper motors or the like, via which movement along the respective axis x,y,z can be independently effected by a joystick or other input arrangement, essentially providing a remote control functionality for positioning the tube S.

In use, the mobile X-ray imager IMA is positioned, via its rollers, sufficiently close to a bed B where the patient PAT lies. The patient is then asked to sit up or, if too infirm to do so, is gently rolled over by medical care staff and the detector D is positioned on the bed's support surface. In one embodiment, the portable detector unit D includes a detector handle to facilitate its positioning. The patient PAT is then either rolled over or asked to lie down so as to essentially cover the portable detector D with the chest or back or other regions of interest. As can be appreciated from the above use scenarios, in particular from the chest X-ray scenario, large parts (or even the whole) of the X-ray detector's radiation sensitive surface itself may not actually be visible to the operator during the imaging, because the patient is lying on it.

Detectors come in various sizes and, for example, a rather compactly built detector may very well end up completely covered and hidden from eyesight when a rather corpulent patient is asked to lie down on same. In mobile imaging there is therefore a serious risk of obtaining sub optimal images, because the mutual spatial configuration of the tube-detector system is not the optimal one for the imaging task at hand. X-ray tube/detector and collimator are likely to be misaligned and or the SID may not be the correct one. The danger of incorrect or imprecise spatial configuration (alignment and distance) of the tube-detector system is compounded by the mobile nature of the detector D because there is no rigid mechanical connection between the tube S and the detector D. There is therefore no permanent, or pre-defined, or a priori known, spatial configuration between the X-ray tube and the detector's image plane as would be the case, for instance, in a permanently installed "C-arm" imager system where detector and X-ray tube are permanently and rigidly mounted in opposed relationship on the respective ends of a rigid yoke-shaped C-arm.

Inset (A) in FIG. 1 shows what can go wrong. It shows an example of an out-of-yaw misalignment, which requires correction by, for instance, rotation of the source S around its z-axis by a correction angle and a translation (not necessarily in this order) in the x, y plane. In contrast, inset (B) shows an example of correct alignment, that is, a line cast through the source's focal point (not shown) will intersect the detector's radiation sensitive surface at its center, and said line is normal to a tangent plane to the radiation sensitive surface at said center point. Said line traces out the line of travel for the central beam or main direction of the radiation beam XB when the tube is in operation. For instance, if the radiation sensitive surface is planar and of rectangular shape (as is indeed the case in some embodiments), then the center point is defined by the intersection of the two diagonals across the rectangle formed by the radiation sensitive surface.

In order to make the task of spatially adjusting the tube-detector system configuration easier and/or quicker, the mobile X-ray imaging apparatus IMA or system as proposed herein includes a navigation-aid subsystem.

The navigation aid includes one or more (radio signal-) reflective markers ("reflectors" or "tags") RFL and (radio signal) transmitter TX and a corresponding radio signal receiver RX to receive the radio signal reflected by the reflectors RFL. There is a transducer TR that converts the received radio signal into positional correction information. This information is so processed that it affords a guiding clue on how to spatially adjust a current or initial tube-detector configuration to arrive, for an impending imaging job, at a desired target (spatial) configuration for the tube-detector system where the required SID and the tube-detector alignment is achieved (both, or at least one of SID and alignment within acceptable error margins). The computer positional correction information can then be rendered in one embodiment by a prompter (processor) PRP into human perceivable sensory form that is suitable to guide the human user how to adjust the tube-detector configuration. For instance, the positional correction information may be rendered visually for view on a display unit, such as a monitor M, or the positional correction information may be modulated into other optical signals, or may be rendered into an acoustic or haptic/tactile form signals. The various sensory forms of the positional correction information may also be combined. The positional correction information and its various sensory perceivable renderings are preferably supplied in real time in response to spatial changes of the tube-detector system to form a data stream. The information is re-computed or updated in the order of milliseconds thereby giving the user the impression of "real time" processing.

In other embodiments, the positional correction information may be fed, instead or, additionally, into a controller CLC that automatically controls an actuator ACC to set the X-ray tube S into motion to so effect in a self-guided manner the desired tube-detector system configuration.

The receiver RX and the transmitter TX are positioned relative to the tube-head S and/or its housing SH. For example, in one embodiment, the receiver RX and/or the transmitter TX are placed on the housing SH, or are otherwise integrated into the X-ray tube head mechanism as will be explained for one embodiment with reference to FIG. 6 below.

In one embodiment, the receiver and the transmitter are combined into a single device in a single housing, or are arranged on a single circuit board to form a transceiver TXRX.

In one embodiment, the transceiver is arranged within or on the tube housing SH.

More generally, in some embodiments, the arrangement of in particular the receiver RX is such that a motion of the X-ray tube/housing (or at least secondary a motion in a known functional relationship to the tube motion) is likewise conferred to either the receiver RX or the transmitter TX. For instance, in one embodiment, tube position and orientation is mechanically connected or coupled to the receiver RX or transmitter TX (or transceiver TXRX) to ensure that the position and orientation of the tube S can be detected.

The one or more signal reflectors or "tags" RFL are affixed to the detector D body to be aligned and sought out. However in some embodiments, the arrangement can be reversed and it is the transceiver TXRX or the separate receiver RX that is arranged in or at the detector plate D ("patient-side") whereas it is the one or more reflectors that are arranged in or at the X-ray tube S or the X-ray tube housing SH.

In yet other embodiments, the transceiver TXRX and or the receiver RX and or the transmitter TX are placed at a suitable position on a wall or a stand or is in fact placed on the ceiling. The whole of the tube-detector system can then be monitored from an elevated position.

No matter the placement scheme used, it needs to be ensured that a coordinate frame, as defined either by the TX, the RX, or the TX/RX must have a "deterministic" spatial relationship with the coordinate-frame of the X-ray tube (see FIG. 1 for the coordinate frame of reference of the X-ray tube S), that is, if one frame is known, the other frame can be computed by suitable transformations.

During operation of the navigation subsystem, the one or more reflector tags RFL may be "pinged" or "sought out" by the transceiver TXRX or the transmitter TX by emitting an electromagnetic (EM) radio-pulse. The transceiver TXRX or the receiver RX then "listens" for an echo from the reflector. The transducer TR then processes the reflected signal or signals (as received at the receiver RX or transceiver TXRX) into a current (instant) position/current distance and/or current orientation information of the detector D relative to the X-ray source S. In one embodiment, this can be done by evaluating the amplitude of the echo signal ("how loud is the echo?") or by evaluating the phase shift (or the "time-of-flight") of the echo relative to the TX or TXRX emitted signal.

The prompter PRP forms a further stage in the signal processing chain, and operates to convert the current position and/or distance and/or orientation information into the positional correction information that needs to be applied to the current detector-tube configuration to attain the target configuration.

Depending on the number of transmitters TX/receivers RX and/or tags RFL used, the positional correction information can be resolved at different levels to obtain more detailed information at increased complexity and cost. For instance in one embodiment, it is only unresolved for whether or not the target is at an expected location, and if not, the positional correction information merely indicates that the motion of the X-ray tube is required, whether manually or automatically. At a more detailed level, it is resolved for whether the target RFL is to the left, is to the right or is above or is below and/or is too close and/or is too far (relative to the tube's position). The positional correction information then indicates the direction of the respective corrective translations that are required. For instance, it is established that the target RFL is not at the expected location but is too far to the right, this is indicated to the user by prompter PRP.

Finally in one embodiment, the positional correction information is resolved down to actual distances by specifying the amounts by which the corrective motions need to be applied. For instance, if the target is not at the expected location but, e.g. is at 120 mm to the right, the positional information indicates that a corrective move to the left by 120 mm is required. The dimensions used herein are non-limiting and are used merely for illustrative purposes.

Various embodiments and variations of the above will now be explained with reference to the following FIGS. 2-10 and 12.

Figure 2:
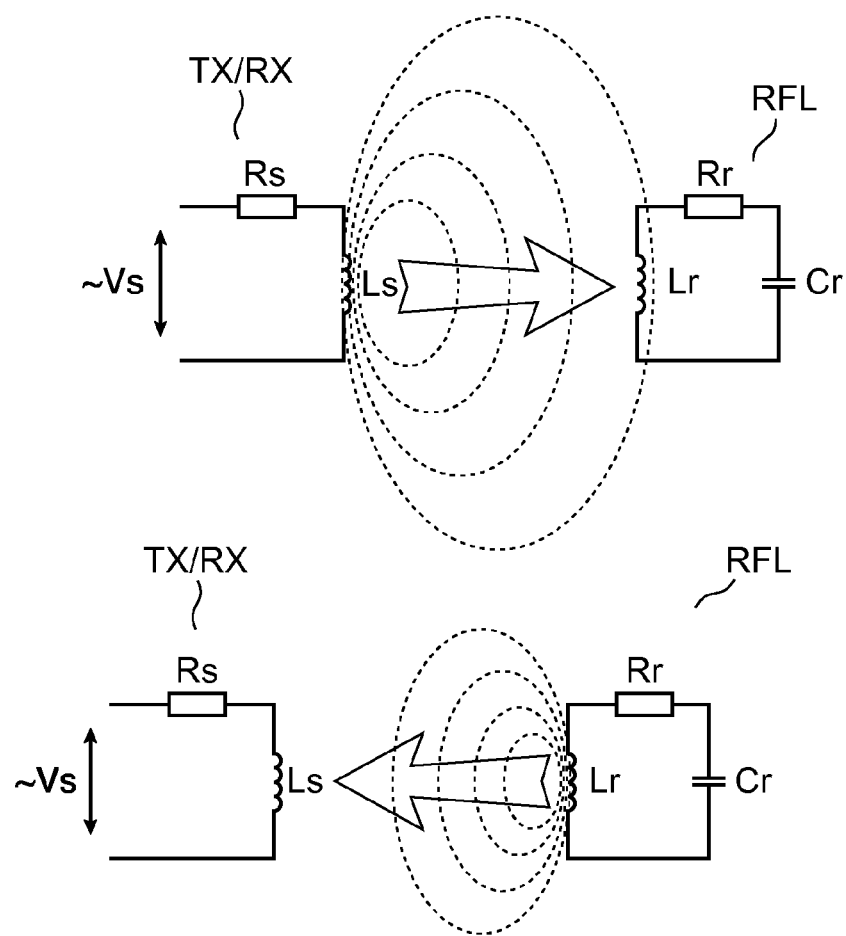
FIG. 2 shows a transceiver and a reflector of the navigation aid subsystem.

With reference to FIG. 2, there is schematically shown a transceiver TXRX that is excited at a certain (predefined) frequency. If the reflector RFL is tuned to this frequency and is present in a working range, said reflector RFL will start oscillating, and thus also emitting electromagnetically, that is, the tag RFL will electromagnetically reflect off the radio signal emitted by the transceiver TXRX. The receiver RX or the receiver component of the transceiver TXRX then picks up this "echo" from the reflector RFL.

In its basic form, the tag RFL is arranged as an LC tank circuit in which an inductance Lr (inductor) and a capacitance Cr (capacitor) are connected in a loop. The LC tank components are arranged on or are embedded in a substrate. In a preferred embodiment, the tag RFL is "passive" in a sense that there is no microchip or IC circuitry on the substrate, and/or there is no autonomous on-board power supply.

The reflector's components may be arranged as a printed inductor and a printed capacitor, not unlike the construction used in anti-theft tags.

The reflectors RFL may even be configured to respond only to a specific, in one embodiment unique (radio-) frequency to so allow unambiguously interrogating a plurality of tags RFL either separately or concurrently.

The reflector(s) may be arranged as a resonator or may be arranged as a non-resonant component, for instance as a "wideband" reflector.

The transmitter component TX includes a power source Vs to generate the energy for transmitting the interrogating radio signal.

In one embodiment, the tags RFL respond by sending back the reflected signal during a certain response time window. In this case, the receiver RX can be configured to listen to any feedback only when the radio-transmitter TX has stopped emitting the interrogating radio signal. Persisting oscillations of the reflector's resonators are employed here to create a separation-in-time. In another embodiment, the receiver RX can be configured to listen concurrently, i.e., while the transmitter TX is still emitting, for the interrogating signal. In order to avoid the reflector's reflected signal to interfere with the transmitter TX/transceiver TXRX interrogation-signal, a geometric arrangement may be used, so as to take advantage of symmetry etc. in order to make the RX-coil selectively less-sensitive to the TX coil. In yet another embodiment, passive, but non-linear components (such as diodes) can be used to generate harmonics at a frequency different than the transmitters interrogation-ping. Each of these embodiments can be used to avoid signal interference in the signal RX stage caused by proximity to its "loud" transmitter. In other words, the previously described embodiments help isolate the receiver RX from the transmitter TX/transceiver TXRX.

In one embodiment, the reflector is of the "wideband" type. In this case resonance is to be avoided, in particular persistent oscillations are to be avoided that may be caused by a "non-persistent" reflector RFL. There may, however, be a mutual inductance between the TXRX and the reflector. As there are no persistent oscillations in RFL, the RX coil must be arranged to listen while the TX coil is still interrogating. The nominal mutual-inductance between the TX and the RX can be predetermined (and is typically designed to be zero, or very low). The presence of the reflector will disturb this mutual-inductance, which can then be measured (as an indicator of position/orientation of the reflector) and can thus be compensated for by moving, e.g., the reflector to a magnetic flux "deadzone" or to achieve a "null" response orientation as will be explained in more detail below in FIGS. 3-10 and 12.

Although in the following, reference is made mainly to the transceiver TXRX arrangement, it is understood that all of the following is equally applicable for the arrangement where the transmitter TX and the receiver RX are arranged as separate components. Also in the following an exemplary embodiment is chosen where the transceiver TXRX is arranged on the tube side whereas the detector tags RF are arranged on the detector side. However it is understood that this is an exemplary embodiment only and the reverse arrangement is also envisaged, where it is the transceiver that is arranged at the detector side and it is the tags RFL that are affixed to the tube S on the tube side. Also, in the following, the detector D is assumed to be stationary throughout adjustment procedure whereas it is the tube S that is moved about to effect attaining the desired adjustment of the tube-detector configuration.

In one embodiment, when in use, the radio transceiver TXRX or transmitter TX "pings" the tag RFL, and from the response (or the lack of it) the transducer TR computes data that relates to the position and/or orientation of the tag RFL relative to the transmitter TX or the transceiver TXRX. Preferably, both signals can have the same frequency although there are embodiments where there is a frequency change between transmitted and reflected signal, which can be achieved by using non-linear passive components such as a diode in the reflector's RFL circuitry.

Because the positions of the transmitter TX and/or the receiver RX are known and so is the specific spatial relationship in which the tags RFL are affixed to the detector D, the received signal can be resolved up to a desired level of detail into a current position and/or orientation of the tag RFL relative to the transceiver TXRX or receiver RX, with the resolution level of detail depending on the number of the transmitters TX/receivers RXs and the reflectors RFL used. This will be explained in more detail below with reference to FIGS. 4-8. For instance, using a single reflector RFL would allow resolving for 5 DoFs at the most. For instance, in the single reflector RFL embodiment, not all rotations may be accounted for such as a rotation around the z-axis (the direction of travel of beam XR).

Figure 3:
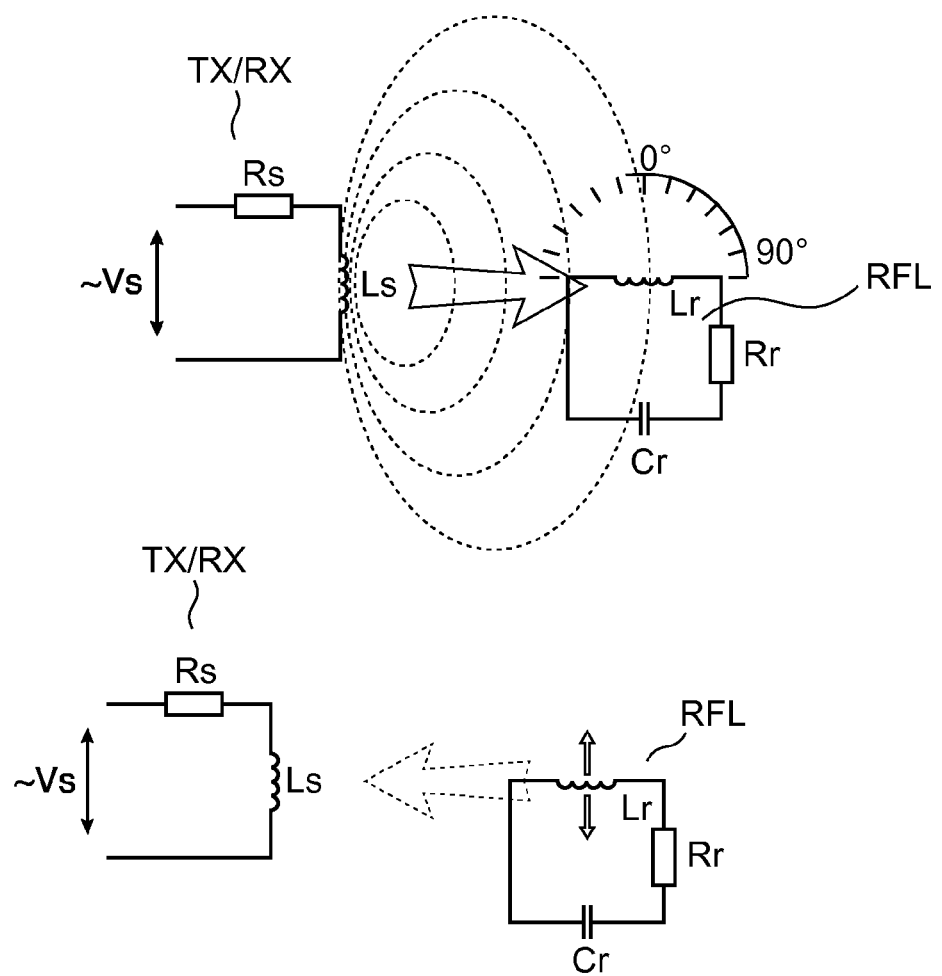
FIG. 3 shows a transceiver and the reflector in various mutual orientations.

FIG. 3 diagrammatically demonstrates the effect of the orientation of the transceiver plane relative to the reflector plane. At certain orthogonal orientations, due to symmetry, the signal coupling between the transceiver TX and the reflector RFL will be zero (that is, there is substantially zero signal strength), thus making, as such, the reflector RFL undetectable. In FIG. 3, a "protractor" shows this "state of orthogonality" orientation diagrammatically in angular terms. As used herein, any two coils are considered to be (magnetically-) orthogonal if the lines-of-flux that one of them produces (as a result of passage of electrical current) are perpendicular to the lines of flux the other would produce (the converse is then automatically also true). It is understood herein, that said state of orthogonality may be realized by the receiver-versus-reflector orientation ("receiver-caused-null-response") or may be caused by a transmitter-versus-reflector orientation ("transmitter-caused-null-response"), or by both. In other words, when in a state of angular orthogonality, the mutual inductance between the two coils is zero by virtue of their mutual angular orientation. However, it is precisely this property that is used in one embodiment to align the relative pitch, yaw and roll of the tube-detector system by seeking out precisely those "null response" configurations that are due to orthogonality. See FIG. 12, where a roll around z-axis can be detected when there is an out of alignment configuration. The response at the receiver RX or the transceiver TXRX will be zero only when the two coils are orthogonal (as shown). To ensure orthogonality at the desired alignment, one may (as shown) run the transmitter's coil along an x axis (that is, its coil windings are around said x axis) and one runs the reflector's coil along a y axis. If there is rotation around the z-axis, the receiver RX will register a signal thereby indicating that the detector D and the tube are out of alignment. It will be understood that this is merely an illustrative embodiment and other suitable arrangement of the TX or RX coils versus the reflector RFL coils may be used to make rotations about axis of interest detectable. It is to be noted, that the scheme in FIG. 12 affords an unambiguous guidance towards the desired tube-detector configuration (in this case, alignment around the z-axis) as there is a zero response when tube-detector system is rotated into alignment around the axis z, and there is a non-zero response if there is a tilt. Although the response curve has a peak where the correction-direction may be ambiguous, this peak will occur only at a huge tilt (of about 90°), which will make it easy for to the user to see that this cannot be the intended configuration, because (for instance in the embodiment where the tube S is movable) dragging the tube XR in the wrong direction would make it point "away" from the patient PAT.

Figure 4:
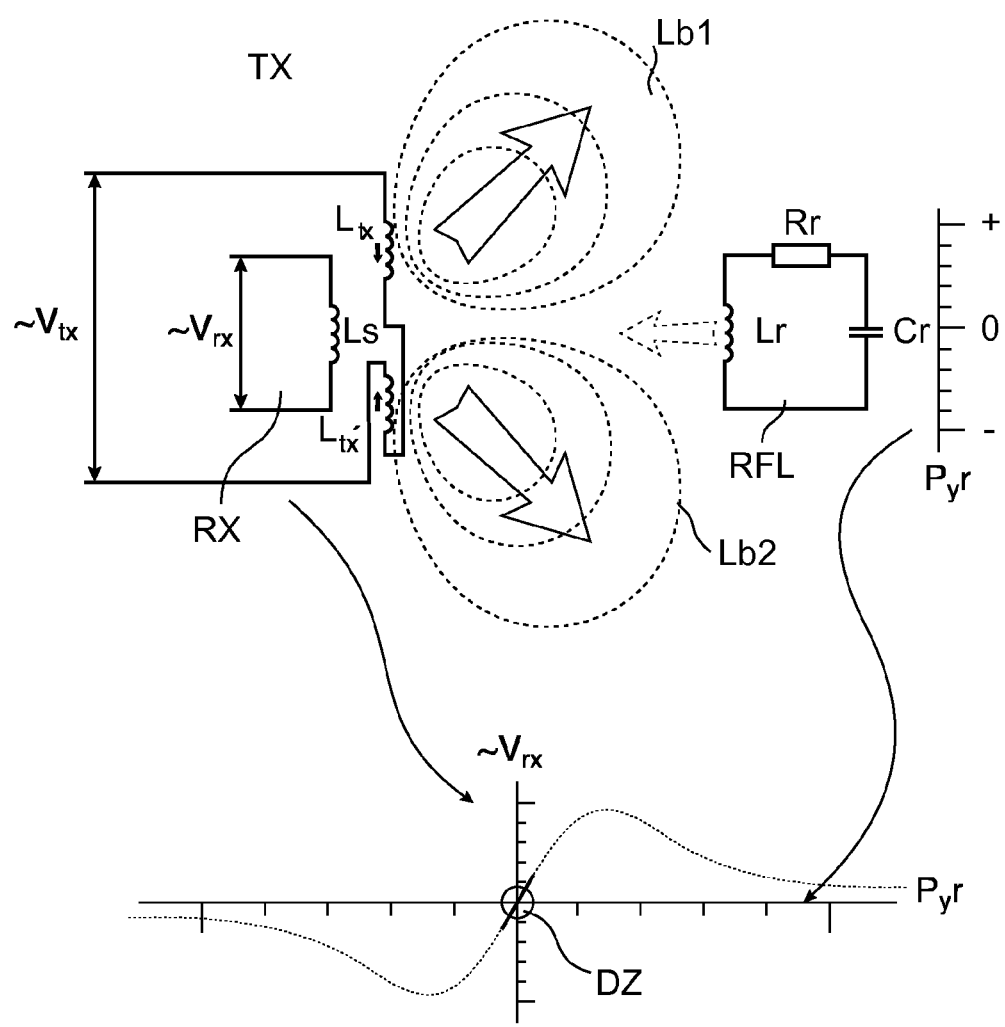
FIG. 4 shows a radio signal reflected off the reflector and received at the transceiver and how said signal varies as a function of the mutual position between and transceiver.

With reference to FIG. 4, there is shown a transceiver TXRX with a multi-coil transmitter component in a single coil receiver component. More specifically, a pair of anti-parallel transmitter-coils are used, Ltx and Ltx', which allows defining a locus-plane of symmetry where the effect of the two coils is equal and opposite. The plane is defined in FIG. 4 as extending perpendicularly between the two lobes Lb1, Lb2 of magnetic flux lines. In other words, any reflector RFL centered upon this plane will also be ineffective, so no signal will reflected. The locus plane thus defines an example, according to one embodiment, for a null response or dead zone.

Another, but "pointwise" (that is, artificially created spots of zero magnetic flux in space) example of a magnetic flux-deadzone will be explained below at FIG. 9, which is harnessed to even determine distance in absolute terms. The deadzone plane of FIG. 4 is based on symmetry of the flux lines and affords a centration of the reflector RFL. This transceiver configuration affords a two DoFs alignment capability where the reflector RFL can be aligned in translation directions x and/or y. The two anti-parallel transmitter coils arrangement is an example of a "phased antenna array" as used herein. Various other implementations using phased arrays are also envisaged in some embodiments, as will be explained below with reference to the phased-array arrangement in the embodiments of FIGS. 6-9.

With further reference to FIG. 4, as the relative position of the reflector RFL along the y-axis ($P_y r$) changes either by moving same or the tube S, the intensity (and phase) of the echo changes (see the illustrative graph). The receiver-coil picks up the echo—positive if the reflector is "up", negative if the reflector is "down" and zero if the reflector is in the middle between signal lobes Lb1,2 on locus plane. This received signal can give information about the necessary position-correction. A similar observation holds true if two or more coils are used with a locus place perpendicular to the one in FIG. 4. One can then likewise adjust along x-direction Pxr. In other words, the tube-detector alignment can be resolved down to two translational DoFs. The signal strength representative of the deviation of the tube-detector configuration from the null zone in either of the two directions then forms the position correction information. In other words, in this deadzone seeking embodiment, it is the degree by which the tube-detector configuration deviates from the null zone that is then modulated by the transducer prompter processor circuitry into an audio, visual or tactile signal as will be explained in more detail below. This modulated signal then furnishes to the user a "clue" or guidance to modify the tube's alignment to the detector. In other words, in the exemplary FIG. 4 embodiment, by i) "strategic" placement of transmitter TX or the receiver RX on or relative to the tube S, and by ii) "strategic" placement of the reflector(s) RFL at the detector D, and by iii) observing the "orthogonality" criterion when placing the tags RFL relative to the TX, RX, the resulting "null responses" can be beneficially used to align the tags RFL (and thus the detector D) with the tube S.

The graph in FIG. 4 plots the received signal strength and polarity versus the $P_y r$ deviation. The polarity gives a clue as to the direction of the corrective action that needs to be applied to the tube position. Alternatively, "nulls" can be strategically created at arbitrary locus-planes by a combination of transmitter intensities and/or phases. As can be seen in the curve of FIG. 4, when one leaves a deadzone DZ to the left or right, the received signal peaks and then dies off asymptotically along the $P_y r$ axis. A "false" movement away from the DZ can be avoided in most cases because one will have to move very far off from the desired configuration which the user will be able to recognize from common-sense that he or she is moving the wrong way (that is, away from the deadzone).

Figure 5:
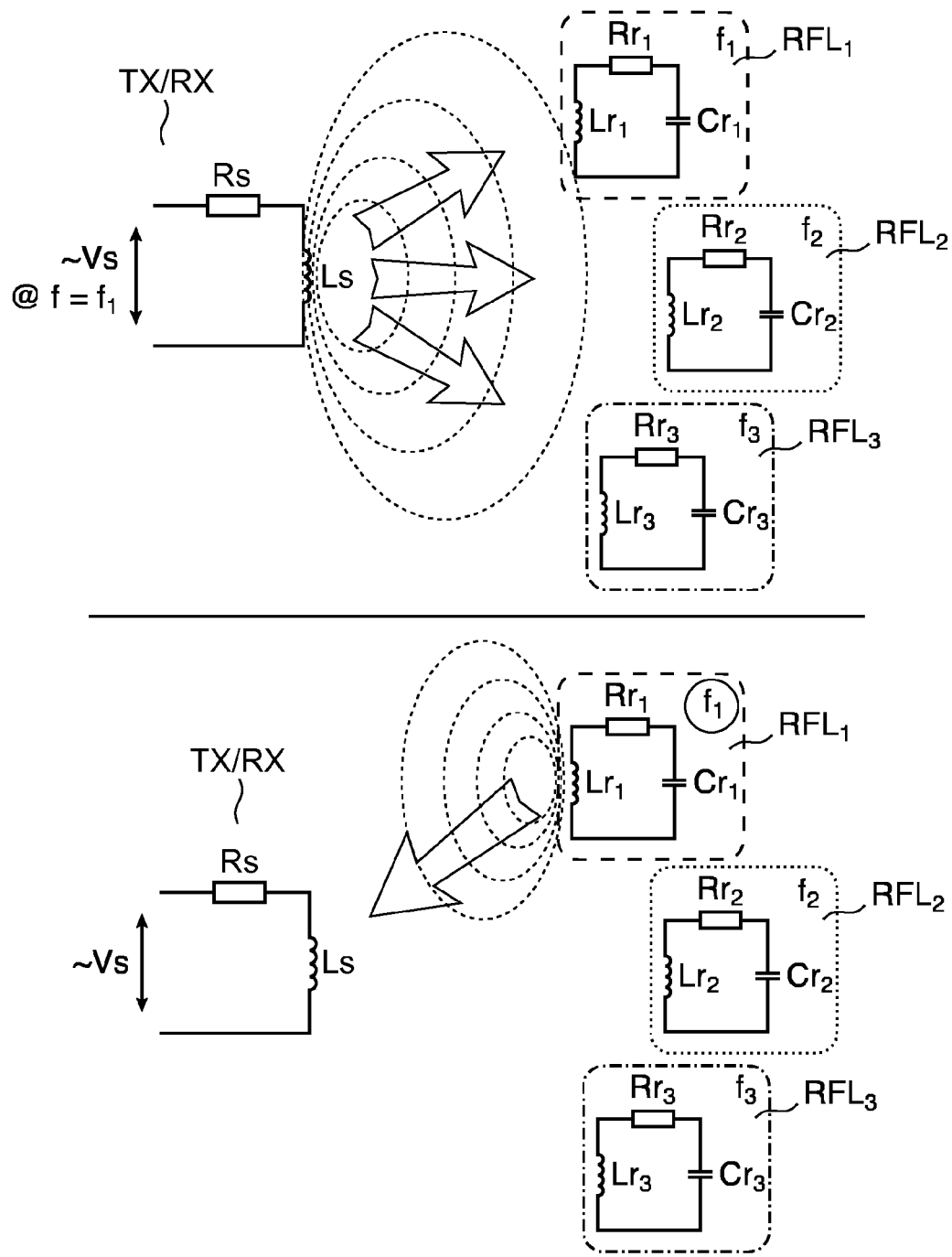
FIG. 5 shows a transceiver in an arrangement with a plurality of reflectors.

FIG. 5 shows schematically a multi-reflector arrangement. Each tag RFL is tuned to a unique frequency and responds exclusively to said frequency. By choosing an appropriate transceiver-frequency, a single one of the reflectors from the plurality of reflectors RFL can be selectively interrogated/pinged. As such, the multitude of tags RFL can be uniquely "addressed" by selecting an appropriate transceiver frequency. In one embodiment, the detector unit D will carry several uniquely responding tags RFL, strategically positioned upon on said detector D. This allows then the detector's position and orientation to be measured relative to the transceiver (and hence the X-ray source) in up to six degrees of freedom. Examples of multi-tag placements are shown below in FIGS. 8a,b.

"Strategically positioned" as used herein means in control-engineering terms to "maximize observability". This may include choosing placements for the reflectors RFL and/or the transceiver TXRX, or the receiver RX, or the transmitter TX to avoid or minimize interferences, for instance placements away from metallic objects, bed-posts, etc. The anti-scatter-grid ASG of the detector may be another source of interference. This ASG caused interference may be mitigated by having an ASG-construction such that electrical "loops" are avoided in its construction, for instance by insulating the ASG's vanes or fins from each other to avoid formation of eddy currents etc. Alternatively, the reflectors may be placed at a location away from the ASG, for instance on the detector housing, but as far away from the ASG as possible, as shown for one embodiment on FIG. 8b on the right. In one embodiment, the ASG is formed from aluminum for instance and not from ferro-magnetic material or lead, or is formed from non-metallic materials. Also, in furtherance of the objective for strategic placement, using a plurality of reflectors, with each reflecting off only at a predefined frequency, allows implementing a "sanity check" or serve as redundancies for the detected signal to ensure that all reflectors are present and to distinguish from unwanted or parasitic reflections. In this embodiment, the transducer TR stage includes a logic circuitry to process the received signal for its trustworthiness. For instance, the signals may be judged sound only if a unique, predefined frequency-combination from the plurality of reflectors is detected. A specific combination of reflector-frequencies may constitute a unique "barcode" to identify a particular detector-device. The plurality of reflectors may be useful in case the environment makes it impossible to receive a signal from a particular reflector (either due to radio-occlusion or due to strong parasitic resonances) so there still exists at least a second measurement point or option.

Figure 6:
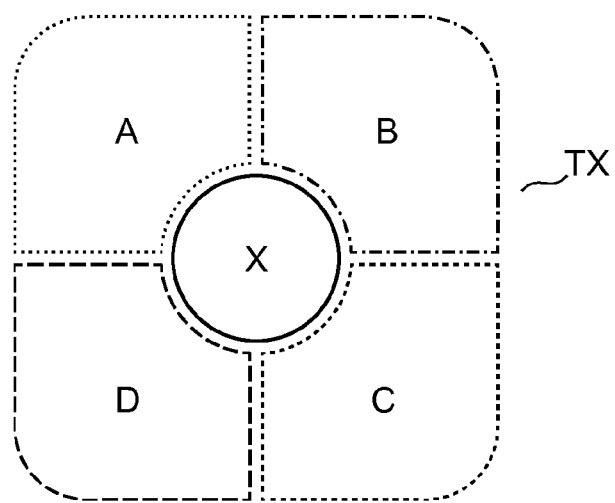
FIG. 6 shows a multi-coil transceiver arrangement.
Figure 6:
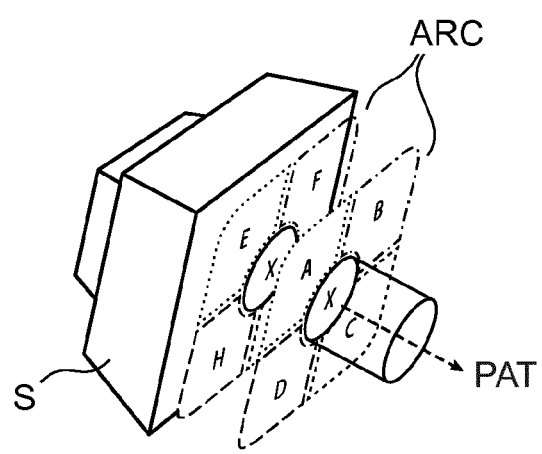

FIG. 6 is an exemplary embodiment for a "smart" geometry for transceiver coils arranged around the tube S. Four transmitter coils A, B, C, and D of the transceiver TXRX are placed in a first array ARC around the X-ray emitter-aperture X, so as to make maximum use of the available area. This quadrant-configuration will allow discriminating of the reflectors RFL in the "up-down" direction as well as the "left-right" direction. In one embodiment, there is a further, second set ARC of a quad-coil array adjacent and parallel to the fist array. This adds resolution capability for more DoFs to the layered phased-array arrangement of tube head S thereby bringing the DoF resolution capability of the FIG. 6 embodiment to 3 DoFs. In FIG. 6, the elements A/B/C/D represent for instance four plastic formers each with a groove running as per the dotted line (or as a circle) and then a current-carrying electric-conductor (one or more turns) are run in the respective groove. In other embodiments, the coils are arranged as a PCB coil or the former is a molded plastic cage to hold (for instance copper) wires. There is also a feed line (e.g. a twisted-pair) feeding the said current to these coils. FIG. 6's upper part shows a plan view of the four coils along their longitudinal axis (that is, the axis around which the coil is wound), with magnetic flux lines are perpendicular to the paper plane. In FIG. 6's lower part, the respective coils, for instance F and B, have their axis parallel and are arranged one behind the other. Although in FIG. 6 the eight coils are illustrated to be parallel, this is a mere exemplary embodiment and different coil-shape and/or coil-assembly, not necessarily parallel, are also envisaged herein resulting in a different flux-density pattern.

Figure 7:
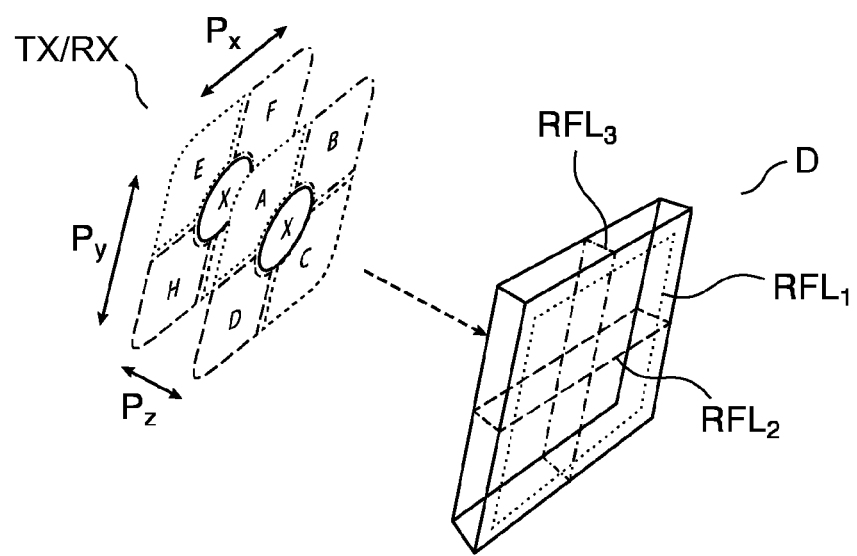
FIG. 7 shows a superimposed or overlapping multi-coil reflector arrangement.

FIG. 7 shows more details of the layered phased-array arrangement of FIG. 6. In one embodiment, implementation of the phased-array is by selecting different polarities when energizing the individual coil-elements. For example, driving coil combination (A+B) with a sinusoidal signal +i, and at the same time driving coil combination (C+D) with a sinusoidal signal −i, the respective tag RFL3 loop (and thus detector body D) can be "centered" in the up/down direction Py. Similar centrations for each DoF around the respective planes can be achieved by driving (with opposed polarity), the coil groups:

(A+D) and (B+C) to center along left-right direction Px;
(A+B+C+D) and (E+F+G+H) to center in a "front-back" search along Pz.

The arrangement of FIG. 7 takes the centration idea of FIG. 4 (which shows an exemplary centration around one plane) further, because FIG. 7 allows centrations around multiple planes.

In FIG. 6, the A,B,C,D coils could be driven with a "rotating" waveform ("Mexican wave"), that is, the coils are driven with four sinusoids, one for each. The four sinusoids have the same frequency, but are 0-90-180-270 degrees apart in terms of their phase. This creates a rotating "seeker" field, and would give zero response from a reflector coil that is exactly centered upon the rotation-axis. However, the above four coil arrangement A+B+C+D or E+F+G+H is merely an exemplary embodiment, and phased array arrangements with fewer (or more than) than four coils for each layer may be used instead.

Figure 8A:
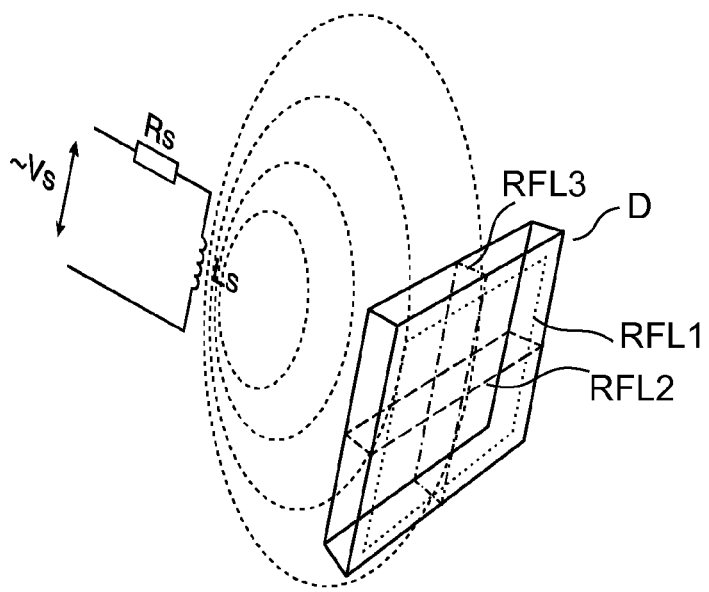
FIG. 8 shows various embodiments of a detector including one or more reflectors.
Figure 8B:
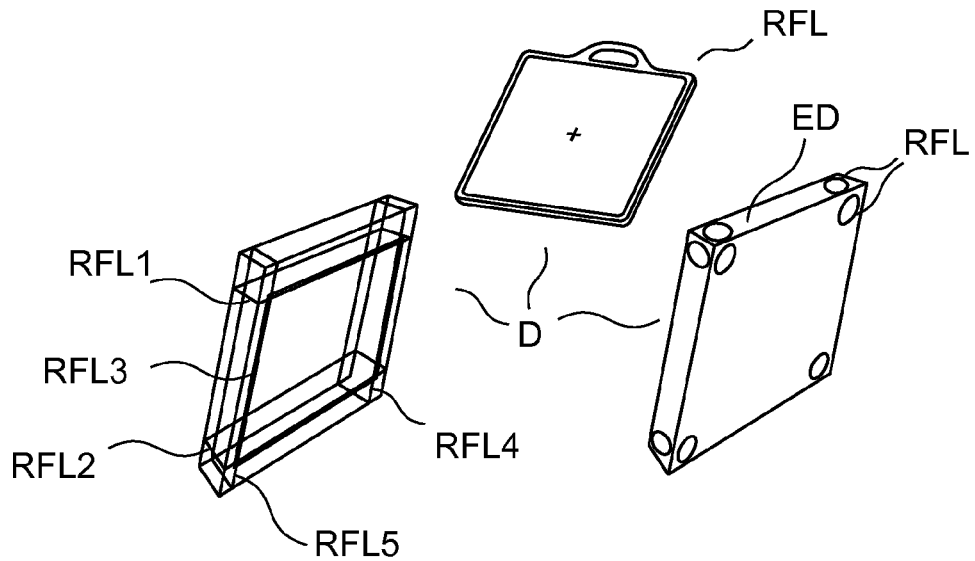

FIGS. 8a, b show examples for reflector-coil RFL placements on, or relative to, the detector plate D. In this embodiment of tag RFL placements, only reflector-coil RFL2 can "talk" to the transceiver when properly centered because of orthogonality as explained above in relation to FIG. 3. The other two coils RFL1 and RFL3, each being orthogonal to TX's inductance Ls, remain in the instant alignment "invisible" and thus non-responsive so no signal is received at RX from tags RFL1 and RFL3. In this embodiment, the three tags RFL are arranged as loops where each one is orthogonal to the other two.

The coils RFL 2,3 are not necessarily arranged or wound around the sides of the detector device D as indicated in FIG. 8. This is merely an exemplary embodiment.

In alternative embodiments, the reflector-elements RFL are "split" up and are spread out for instance as small patches and positioned so as not to occlude the radiation sensitive-area of the X-ray-detector D. This is shown in the RFL tag placements to the right in FIG. 8B, where the RFL tags are (round or quadrangular or other suitable shape that fits the space constraints at hand) patches that are small enough to fit into corner portions of the detector D's border portions and do not extend into the radiation sensitive areas, but are confined to the border of the detector housing. Placement on the edge surface ED is also envisaged if the thickness of the detector plate so permits. Placements can either be symmetrically or asymmetrically. There is an arrangement to the left of FIG. 8B, where there is a total of five coils used. One is laid out in the detector plane to follow the border portion of the detector whereas the remaining four are arranged into two parallel groups, two coils in each group. Each coil in each group is orthogonal to the border coil, but coils from different groups are wound around the detector body across different pairs of the four detector edges with each coil in each group confined to the respective detector border portions.

The one or more tags RFL may be affixed to the tube S or the detector D via adhesive stickers arranged in the tags, or via clip-ons or are screwed or bolted to the detector D body, either permanently or irremovably. In one embodiment, detector includes tracks formed in the housing to slidably receive therein the tags RFL, which are suitably formed to match the tracks. The tags RFL may be integrated inside the detector housing (so are not visible for a human observer) or are arranged to the outside, on the detector housing.

Figure 9:
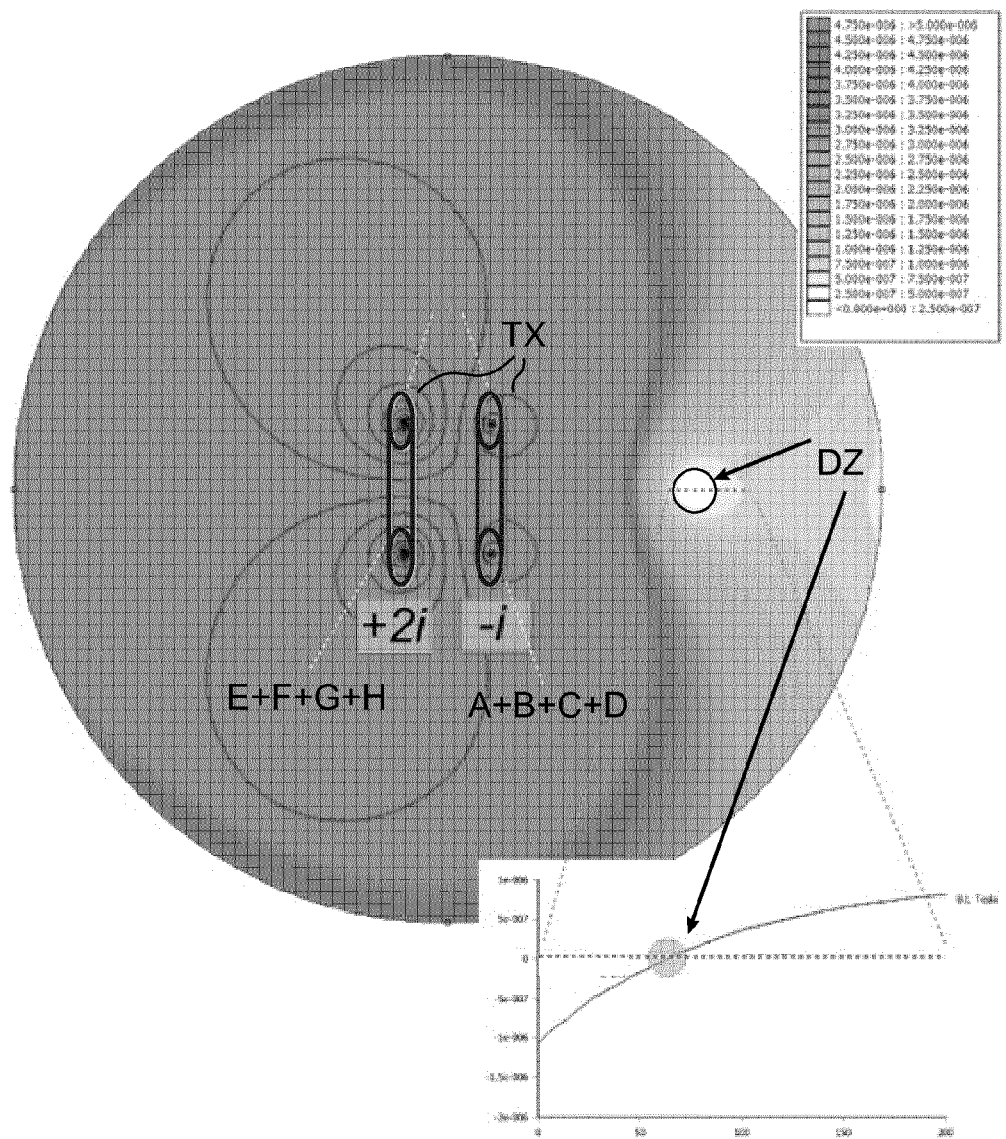
FIG. 9 shows a magnetic flux plot around the vicinity of a multi-coil transceiver.

FIG. 9 shows a phased array configured to seeking a null or deadzone as per FIGS. 4, 8 for absolute positioning and not merely for centering and alignment. In this exemplary embodiment, two effective coil groups A+B+C+D and E+F+G+H are "back-to-back" and parallel similar to FIGS. 6, 7 where each coil group is driven by opposite currents in a particular ratio, say +2i and −i. FIG. 9 shows a view of the coils with their longitudinal axis and the magnetic flux lines parallel to the paper plane. In other words, FIG. 9 shows phased-opposed parallel transmitter TX (or in one embodiment, transceiver TXRX) coils.

Depending on the geometry of the coils, this arrangement results in formation of a "null" spot DZ at a particular distance from the coils (and a second vestigial 'null' spot between the two coils). This comes about as these two coils are in opposition. The magnetic field strength B along the axis of a coil drops as the inverse-square of the axial-distance. At a (far) distance, the coil that carries more current will be dominant. At a near distance, the other (weaker) coil will become dominant, due to proximity. This creates exactly two null points along the common-axis where an absolute value |B| of the magnetic field is exactly zero. One of these null points, the vestigial null spot, must lie between the two coils and is not of interest here. The other null spot or point lies outside of the two coil groups and on the side of the (weaker) coil. This is a direct consequence of Biot-Savart law, whereby the magnetic flux-density is inversely proportional to the distance-squared. Both null points lie upon the (common) axis of the coils. If reflector RFL is closer to the transceiver than this spot DZ, the nearer (−i) coil is more dominant, resulting in a negative phase on the echo. If the reflector is too far, the other coil (energized at +2i) becomes the dominant one, in which case the reflected signal will have a positive phase (i.e., is "in-phase" with the +2i signal). Exactly at the "null" point DZ, the magnetic flux that is caused by the two transmitter-coil systems, cancel each other at deadzone spot DZ. This is shown in the flux density plot in FIG. 9 where the shading encodes flux densities of field B (in Tesla) with zero density at spot DZ. While this technique is very effective for seeking out a position along an axis (here, the z-axis), it may be less effective for seeking out a position along other directions. Therefore, to resolve for more DoFs, the FIG. 9 embodiment may be combined with the embodiment of FIG. 4. For instance, one may use time-domain multiplexing (for instance, as previously explained in the "Mexican wave" driving scheme in relation to the embodiment of FIG. 6) to find the in-plane centration shifts left/right/up/down search as per FIG. 4 to axially-align the tube S and the detector D. Once this is done, the user is invited to shift along said axis to search for the deadzone as per FIG. 9 to set the correct source-detector distance. The prompter PRP may operate to guide the user to now adjust moving only along the center axis z, for instance, by modulating an audio/visual or tactile signal according to deviations from said axis. If the user deviates too far off, more iterations as per FIG. 4 might be needed to re-center once more.

The polarity of the reflected echo is an indication for the desired direction of correction. Furthermore, the ratio of the current-amplitudes i1, i2 that are used to respectively energize the two coils may be adjusted to "nudge" the dead-zone DZ along the z-axis to adjust for a desired SID for a particular (different) detector, or, to extend the reach to search over a wider area for the presence of reflectors RFL.

A distance vs. flux graph is plotted for illustration at the lower right of FIG. 9, where the different polarities (+/−) can be used as indication for the suggested direction of correction. A received signal with a negative phase (compared to the signal '+2i') indicates that the RFL is too close whereas a positive phase-value indicates that tag RFL is too far. In one embodiment, the magnetic flux values are given out as positional correction information and the values are updated in real-time in response to changes to the tube position/orientation. In a simple trial-and-error manner, the user can then tentatively move the X-ray tube to get a sense for how the magnetic flux values (and in particular their polarity) changes with positional changes of the X-ray tube head. In this manner the user is then guided towards the desired tube-detector configuration by observing the real-time displayed magnetic flux values and carefully moves the tube head about until the flux is cancelled at a sufficient degree. So even if no directional clue is given, users can still trial-and-error their way to the deadzone. When the polarity of the received signal (that is, the polarity of current in the receiver coil induced by the received radio signal) is processed and modulated and given out for the user or tube motion control CLC, a more detailed correctional clue can be provided, because now the user is informed about the direction the translation or rotation he or she is supposed to apply to approach the deadzone.

Comparing FIG. 4 with FIG. 9, in FIG. 4 a locus plane is created where magnetic flux component Bx is zero due to symmetry. This allows localizing a direction/centration, but not a distance. The embodiment in FIG. 9 in itself, allows forming, by tuning currents and their polarity, a deadzone (with zero flux due to inverse-square or inverse-cube drop-off) point to so "peg" a distance in absolute terms. There is no response from the reflector coil when the reflector coil passes through said deadzone spot DZ, no matter its orientation. By combining the FIG. 4 and FIG. 9 embodiments (the phased array in FIG. 6 is an exemplary embodiment for such a combination) one can achieve centration and positioning at a desired distance although either one of the FIG. 4 or FIG. 9 may be used in some embodiments without the other if a lower DoF resolution is sufficient for the task at hand. In one embodiment, the navigation aid subsystem may include a user interface (shown in monitor M or a dedicated LCD display or similar integrated in the imager) that invites the user to change polarity and/or ratio to effect search of nulls at a select distance to adjust navigation aid to the imaging task at hand. A setup GUI may be used in one embodiment, which is displayed (at least initially) on screen M to invite the user to supply via click-boxes, drop-down menus or other suggestive GUI widgets the SID specification for a particular detector-device. Other user-input means such as keyboard where the user types the SID to be used for the current imaging session is also envisaged in simpler embodiments. The supplied SID is then mapped to the corresponding coil polarities and amplitudes to accordingly energize transmitter/transceiver emitter coils.

In an alternative embodiment, a simulation plot similar to the one in FIG. 9 is displayed on a monitor M or dedicated (LCD or otherwise) display unit with a distance gauge overlaid. Alternatively, it is the flux vs. distance graph that is displayed. The user then operates suitable GUI sliders or other input sources to tune the two coil currents. The tuning action is graphically displayed by a marker (shown as a hair-cross, circle or other suitable marker symbol) that moves over the plot or graph until the deadzone marker assumes the desired SID for the detector with the ASG. The corresponding current values/polarities are then forwarded to a coil control circuitry to effect setting the selected coil currents. It should be understood that there could be a certain initial setup effort required after fitting the navigation aid as proposed herein to an imaging apparatus. In the setup procedure, it is ensured that by adjusting polarity and current amplitude of transmitter/transceiver and by proper orthogonal placement of transmitter/receivers and the tags RFL, the deadzone is formed at the required SID and at an acceptable alignment. The navigation subsystem is thereby initially setup to an acceptable spatial target configuration of the tube-detector system and this target configuration can then later be "retrieved" or "re-found" when processing the reflected radio signal to find the signal deadzones DZ and the proper mutual orthogonal orientation between tags RFL and the transceiver TXRX or the transmitter TX, or the receiver RX.

Figure 10:
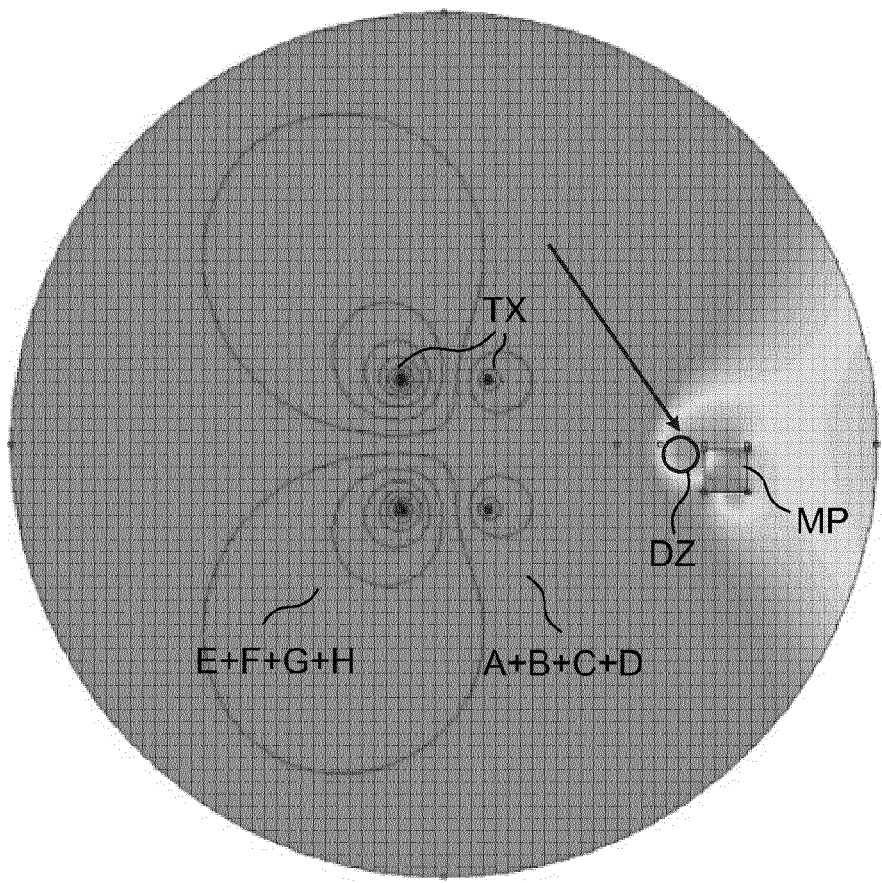
FIG. 10 shows a magnetic flux plot around the vicinity of a multi-coil transceiver and a metallic object.

FIG. 10 is based on the simulation data as per FIG. 9, and demonstrates that the absolute position of the resulting "null" point DZ is reasonably insensitive to the presence of magnetic parts MP (in this example stainless-steel) in the vicinity of the reflector RFL. This indicates that the proposed navigation aid subsystem can be robustly used in typical clinical environments where (ferro-) metallic objects abound, like bed parts, instruments, prostheses etc.

In one embodiment, the prompter includes and drives visual indicators to indicate deviation from the dead zone DZ. For instance, one or more bar graphs each with multiple segments (not unlike the battery charge indicators used in mobile phones for instance) are used, each associated with a respective DoF and coil pair: Each bar graph forms a "DoF channel" as it were and responds by the displayed number of segments (bars) going up or down as the X-ray source is moved about to find the desired tube-detector configuration. Dead zone proximity can be encoded by displaying more bar segments as the tube-detector configuration approaches the target configuration where the corresponding deadzone is detected by the receiver RX-transducer TR circuitry. The reverse is also possible so that less and less bar segments are displayed as one approaches the deadzone or state of mutual orthogonality. The user then adjusts the tube position, until for each of the monitored degrees of freedom, the respective bar graph has vanished or the maximum number of segments is displayed for each DoF.

The visual indicators as supplied by prompter PRP can be rendered for viewing on a separate LCD display or as a virtual GUI rendered as status icon display on the console's monitor M. The console monitor M or the separate display unit is arranged such that user can easily inspect and keep an eye on same whilst moving the tube. For instance, if the console monitor M is used, an articulated monitor holder arm is attached in one embodiment at one end to the imager IMA's undercarriage UC while the other end receives the monitor M. The monitor can thereby be moved into a convenient position so the visual clues supplied by the prompter can easily be observed when adjusting the tube's position. Similarly, in the embodiment with separate prompter display (implemented as a small LCD display unit), this may be embedded at an easy to inspect location in the imager's housing or may be integrated in the tube head housing.

In one embodiment, the prompter PRP circuitry includes and drives a speaker system and operates to modulate loudness and/or pitch of a sound in accordance with the required positional correction information, that is, with motion of tube or detector. The closer the tube-detector system is to the desired target spatial configuration, the louder the sound or the higher the pitch or inversely, loudness wanes and or pitch lowers the closer tube-detector system is to the desired target spatial configuration.

In one embodiment, the prompter haptic/tactile modulation is envisaged, where, with suitable electromagnetic means, mechanical vibrations at different frequencies are imparted to a user input means with which user controls motion of the tube S. For instance, in the remote control embodiment, the tube motion control joystick is set into vibration or, in the manual embodiment without actuators, it is the handle that is configured to impart vibratory motion to the user's hand whilst the user grabs same to move about the tube. The vibratory frequency of joystick or tube handle is modulated to vary with the position correction information. For instance, vibration frequency increases when the tube is being moved away from the dead zone and decreases when moving towards the deadzone DZ to so nudge the user guided motion into the right direction.

Other visual options are to have a lamp arranged on the housing, carriage or otherwise, whose light intensity varies with signal strength to indicate to user whether he moves tube away from or towards deadzone. Instead of modulating the light intensity in this manner, a flashing frequency may be modulated, or the light's spectrum may be changed across a certain range to suggest proximity to the deadzone DZ. For instance prompter PRP may drive selectively an array of color LEDs emitting light at different spectra. For instance, a suggestive color symbology may be realized by energizing red LED(s) when moving away from deadzone whereas orange and then green LED(s) are energized instead of the red one(s), when approaching the dead zone or the state of orthogonality.

Although the various modulation embodiments have been explained above with reference to the deadzone DZ searching embodiment, it is understood that said sensory signal modulations find equal application in the other embodiments where phase or time of flight or others principles are used to seek out the target RFLs to determine the desired spatial configuration of the tube-detector system.

The frequency or frequencies of the radio signal used herein is or are adapted for medical compliance and are selected to have the required insensitivity to dielectric materials (patient's body). It has been found advantageous to use low-frequency radio signals in the range kHz to MHz range, or more particularly between 30 kHz to 1 MHz.

It should also be appreciated from the above, that the proposed navigation aid subsystem can be conveniently installed as an "add-on" to existing mobile imagers. A suitable number of RFL reflectors will need to be affixed to, for instance, the detector of the imager to be upgraded, and the transducer TR is installed either centrally on a server or on the workstation or console of the imager. Transducer and/or prompter circuitry may also be arranged as standalone devices for instance as suitably programmed field devices. The transmitter TX, the receiver RX or the transceiver TXRX are suitably arranged on or relative to the mobile imager in a setup or installation phase for the specific imaging task at hand.

It will also be appreciated that the embodiment in FIG. 3, where the X-ray imager is shown as a dolly type, is exemplary only. For instance, in a different embodiment, a ceiling mounted embodiment of a mobile X-ray apparatus may be used instead. This embodiment is still "mobile" in the sense that the X-ray tube can be positioned anywhere in the examination room and, in particular, there is still no (permanent) mechanical connection with the mobile detector. In this embodiment there is an overhead carriage fixed to a ceiling of a room. The overhead carriage has an articulated suspension arm. The suspension arm holds the X-ray tube which can then be positioned in manner similar as in the dolly type imager explained earlier. Again, the tube may be positionable by remote control or may be manually "dragged" by user via handle H to the desired position and/or into alignment.

The components of the navigation imager subsystem, that is, the transducer TR, prompter PRP processor and the interfaces to connect to the transmitter TX, the receiver RX (or the transceiver TXRX), may be programmed in a suitable scientific computing platform such as Matlab® and then translated into C++ or C routines maintained in a library and linked when called on by a workstation WS. The components may be arranged as dedicated FPGAs or as hardwired standalone chips. In one embodiment, the components run as software modules on the imager's work station that supports the console. In other embodiments, the software modules are installed on a central server system and the imager's workstation connects as a "client" to same via a suitable communication network if the navigation aid is to be run. In this "thin" client embodiment is envisaged, that the server can support a multitude of mobile imagers in a large medical facility. The transducer TR and/or prompter PRP processor circuitry and the respective output means for the prompter to guide the user (speaker system, flash lights, etc) may be arranged as a separate mobile device or "navigation kit" that is either standalone (so has its own operating system and power supply and/or display (LSD or similar) unit, etc) and/or is connectable with or installable on the imager's console CON/workstation. In the later cause, the console CON's monitor M and/or speaker system (if any) may be used.

It will be further understood that the proposed navigational system may be combined with other positioning/alignment aids such as sensing means to sense the "down" direction with an accelerometer or similar and/or light based "rough-positioning" facilities that use laser-dot/cross/line/polygon or other "cross-hair" light projections that are projected from the tube onto the detector D (if visible) or patient PAT. The accelerometer is used for gravity measurements and can pinpoint the "down" direction to fractions of a degree, and can also supplement the positional correction information (as per the above described embodiments) to help angularly-align (2 of the 3 rotational DoFs) of the tube-detector configuration.

Figure 11:
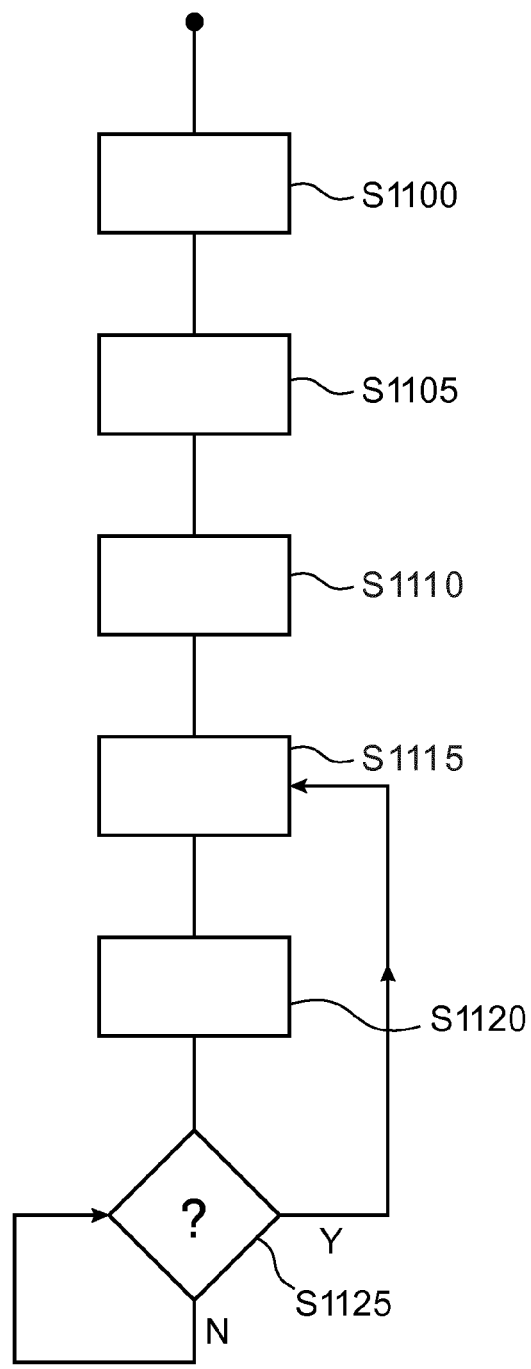
FIG. 11 shows a flowchart for a method of adjusting a tube-detector system.
Figure 12:
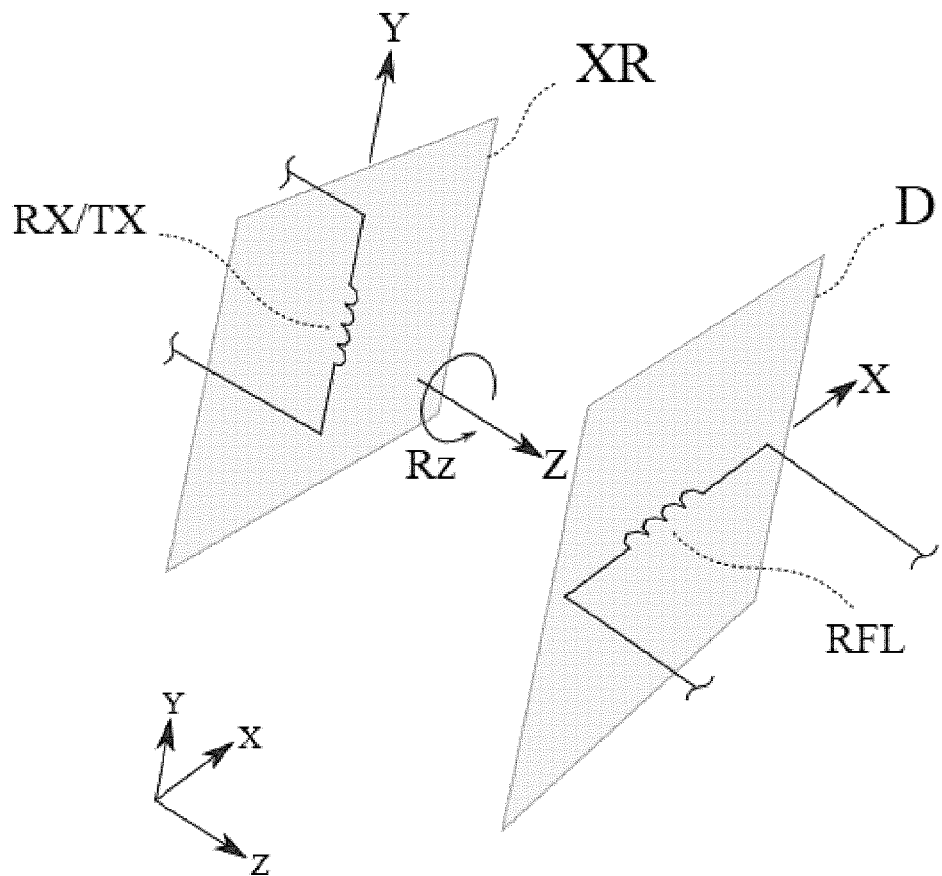
FIG. 12 shows a transmitter and reflector rotated relative to each other.

With reference to FIG. 11, there is shown a flow chart for a method of adjusting the spatial configuration of a tube-detector system of an imaging apparatus. The tube and/or the detector is movable.

In step S1100, an interrogating radio signal is emitted from the transmitter.

In step S1105 the emitted radio signal is reflected off one or more reflector tags.

In step S1110, the reflected radio signal is received at a receiver. A mutual spatial relationship of the transmitter, receiver and the one or more reflectors is such that the reflected off signal is influenced by the motion and/or orientation and/or position of either the tube or the detector, or both. In one embodiment the transmitter and/or receiver are arranged at the tube whereas the one or more tags are arranged at the detector. In one embodiment, the feeding current of the transmitter/transceiver coil(s) is so tuned that the radio signal is no longer received at the receiver when the tube is positioned at a desired distance from the detector and/or is no longer received because there is mutual orthogonality between the reflector coils and the receiver coil, or the transmitter coil, or the transceiver coils when the tube and detector are in (a desired) alignment.

In step S1115, the received signal is converted into positional correction that is suitable to guide a motion of either the tube detector towards a desired target spatial configuration of the tube detector system.

In step S1120, the positional correction information is rendered into a sensory signal form by prompter to invite application of said positional correction information to the tube or the detector. The sensory signal form (audio, tactile, visual or otherwise) is modulated according to the positional correction information to guide the user to apply the positional correction information for instance by moving the tube and/or detector to achieve the desired spatial configuration between tube and detector.

In step S1125, it is then determined ("listened for") whether a further radio signal is received step S1105. If a further radio signal is received, the above steps S1115-S1120 are then repeated to effect an update of the positional correction information and of the prompt.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system, comprising:
an X-ray source;
an X-ray detector configured to receive X-rays from the X-ray source, at least one of the X-ray source and the X-ray detector being movable;
a radio frequency transmitter and a radio frequency receiver mounted to a common housing of the X-ray source and the X ray detector;
a plurality of reflectors, each reflector configured to resonate at a different radio frequency, wherein the radio frequency transmitter is configured to transmit a radio signal configured to cause the reflectors to resonate at different radio frequencies, and wherein the radio frequency receiver is configured to receive radio frequency resonant signals at each of the radio frequencies at which the reflectors are configured to resonate; and
a processor configured to:
receive the radio frequency resonant signals and convert the received radio frequency resonant signals into information indicative of a relative spatial configuration of the X-ray source and the X-ray detector,
determine positional correction information to guide relative motion of the X-ray source and the X-ray detector into alignment a predetermined distance from each other, and
control at least one of (1) an actuator to control the relative motion of the X-ray source and the X-ray detector, and (2) a prompter to issue at least one of optical, haptic, and acoustic signals to bring the X-ray source and the X-ray detector into the alignment at the predetermined distance.

2. The system of claim 1, wherein the positional correction information is supplied in a data stream and updated while the X-ray source or the X-ray detector is being moved.

3. The system of claim 1, wherein the X-ray source or the X-ray detector is configured to be moved manually.

4. The system of claim 1, further comprising a display configured to display the positional correction information or an updated positional correction information.

5. The system of claim 1, wherein the processor is configured to determine the positional correction information based on a signal strength of the received radio frequency resonant signals.

6. The system of claim 1, wherein each of the reflectors has a different position or orientation with respect to each other when the X-ray source and the X-ray detector are aligned at the predetermined distance.

7. The system of claim 1, wherein the radio frequency transmitter is one of a plurality of radio frequency transmitters, said plurality of radio frequency transmitters arranged as a phased array.

8. The system of claim 1, wherein the radio frequency transmitter and the radio frequency receiver are both mounted to the X-ray source, and the plurality of the reflectors are mounted to the X-ray detector.

9. The system of claim 1, wherein the imaging system is mobile, and the X-ray detector is portable.

10. The system of claim 1, wherein the X-ray source and the X-ray detector are movable relative to each other with six degrees of freedom, and wherein the positional correction information is indicative of alignment between the X-ray source and the X-ray detector.

11. A method for adjusting spatial configuration of an imaging apparatus that includes an X-ray source and an X-ray detector, the X-ray detector being configured for receiving X-ray radiation emittable from the X-ray source, the X-ray source and the X-ray detector being movable relative to each other, the method comprising:
   transmitting a radio frequency signal with a radio frequency transmitter of the imaging apparatus;
   reflecting the radio frequency signal by a plurality of reflectors, each reflector configured to resonate at a different radio frequency, wherein the radio frequency transmitter is configured to transmit the radio signal configured to cause the reflectors to resonate at different radio frequencies, and wherein a radio frequency receiver of the imaging apparatus is configured to receive radio frequency resonant signals at each of the radio frequencies at which the reflectors are configured to resonate;
   receive the radio frequency resonant signals and convert the received radio frequency resonant signals into information indicative of a relative spatial configuration of the X-ray source and the X-ray detector;
   determine positional correction information to guide relative motion of the X-ray source and the X-ray detector into alignment a predetermined distance from each other; and
   control at least one of (1) an actuator to control the relative motion of the X-ray source and the X-ray detector, and (2) a prompter to issue at least one of optical, haptic, and acoustic signals to bring the X-ray source and the X-ray detector into the alignment at the predetermined distance.

12. A non-transitory computer readable medium having one or more executable instructions stored thereon, which when executed by a processor, cause the processor to perform a method for adjusting spatial configuration of an imaging apparatus including an X-ray source and an X-ray detector, the X-ray detector being configured for receiving X-ray radiation emittable from the X-ray source, the X-ray source and the X-ray detector being movable relative to each other, the method comprising:
   transmitting a radio frequency signal with a radio frequency transmitter of the imaging apparatus;
   reflecting the radio frequency signal by a plurality of reflectors, each reflector configured to resonate at a different radio frequency, wherein the radio frequency transmitter is configured to transmit the radio signal configured to cause the reflectors to resonate at different radio frequencies, and wherein a radio frequency receiver of the imaging apparatus is configured to receive radio frequency resonant signals at each of the radio frequencies at which the reflectors are configured to resonate;
   receive the radio frequency resonant signals and convert the received radio frequency resonant signals into information indicative of a relative spatial configuration of the X-ray source and the X-ray detector;
   determine positional correction information to guide relative motion of the X-ray source and the X-ray detector into alignment a predetermined distance from each other; and
   control at least one of (1) an actuator to control the relative motion of the X-ray source and the X-ray detector, and (2) a prompter to issue at least one of optical, haptic, and acoustic signals to bring the X-ray source and the X-ray detector into the alignment at the predetermined distance.

* * * * *